(12) United States Patent
Hayward et al.

(10) Patent No.: US 8,420,400 B2
(45) Date of Patent: *Apr. 16, 2013

(54) SYSTEM AND METHOD FOR AUTHENTICATING TABLETS

(75) Inventors: James A. Hayward, Stony Brook, NY (US); Ming-Hwa Liang, Stony Brook, NY (US); Stephane Shu-Kin-So, Middle Island, NY (US)

(73) Assignee: APDN (B.V.I.), Inc., Stony Brook, NY (US)

( * ) Notice: Subject to any disclaimer, the term of this patent is extended or adjusted under 35 U.S.C. 154(b) by 864 days.

This patent is subject to a terminal disclaimer.

(21) Appl. No.: 11/954,055

(22) Filed: Dec. 11, 2007

(65) Prior Publication Data

US 2009/0075261 A1   Mar. 19, 2009

Related U.S. Application Data

(63) Continuation-in-part of application No. 11/437,265, filed on May 19, 2006, which is a continuation-in-part of application No. 10/825,968, filed on Apr. 15, 2004.

(60) Provisional application No. 60/682,976, filed on May 20, 2005, provisional application No. 60/463,215, filed on Apr. 16, 2003, provisional application No. 60/874,425, filed on Dec. 12, 2006, provisional application No. 60/877,875, filed on Dec. 29, 2006, provisional application No. 60/877,869, filed on Dec. 29, 2006.

(51) Int. Cl.
G01N 33/00 (2006.01)
C12Q 1/68 (2006.01)

(52) U.S. Cl.
USPC .............. 436/91; 436/94; 436/164; 252/582; 435/6.11; 442/121

(58) Field of Classification Search ............. 436/91, 436/94, 164; 536/25.3; 435/5, 6, 91.2, 6.11; 252/582; 442/121
See application file for complete search history.

(56) References Cited

U.S. PATENT DOCUMENTS

| 4,183,989 A | 1/1980 | Tooth |
|---|---|---|
| 4,739,044 A | 4/1988 | Stabinsky |

(Continued)

FOREIGN PATENT DOCUMENTS

| EP | 1403333 A1 | 3/2004 |
|---|---|---|
| GB | 2434570 | 6/2007 |

(Continued)

OTHER PUBLICATIONS

Wollenberger, L.V. Detection of DNA using upconverting phosphor reporter probes.(1997). Proceedings of SPIE-The International Society for Optical Engineering, 2895(Ultrasensitve Biochemical Diagnostics II), 100-111.*

(Continued)

*Primary Examiner* — Krishnan S Menon
*Assistant Examiner* — Rebecca M Fritchman
(74) *Attorney, Agent, or Firm* — Algis Anilionis; F. Chau & Associates LLC

(57) ABSTRACT

A method for authenticating and verifying a pharmaceutical item to be genuine is described. The method for authenticating a tablet comprises applying a particular nucleic acid material associated with a particular sequence of nucleic acid bases to a tablet or capsule. The method also comprises collecting a sample of the tablet and verifying the tablet is genuine by detecting the particular nucleic acid material.

30 Claims, 5 Drawing Sheets

U.S. PATENT DOCUMENTS

| | | | |
|---|---|---|---|
| 4,757,141 | A | 7/1988 | Fung et al. |
| 5,047,519 | A | 9/1991 | Hobbs, Jr. et al. |
| 5,132,242 | A | 7/1992 | Cheung |
| 5,139,812 | A | 8/1992 | Lebacq |
| 5,151,507 | A | 9/1992 | Hobbs, Jr. et al. |
| 5,429,952 | A | 7/1995 | Garner et al. |
| 5,602,381 | A | 2/1997 | Hoshino et al. |
| 5,639,603 | A | 6/1997 | Dower et al. |
| 5,763,176 | A | 6/1998 | Slater et al. |
| 5,776,713 | A | 7/1998 | Garner et al. |
| 5,866,336 | A | 2/1999 | Nazarenko et al. |
| 5,942,444 | A | 8/1999 | Rittenburg et al. |
| 5,989,823 | A | 11/1999 | Jayasena et al. |
| 6,030,657 | A | 2/2000 | Butland et al. |
| 6,057,370 | A | 5/2000 | Weiland et al. |
| 6,127,120 | A | 10/2000 | Graham et al. |
| 6,140,075 | A | 10/2000 | Russell et al. |
| 6,169,174 | B1 | 1/2001 | Hasegawa et al. |
| 6,312,911 | B1 | 11/2001 | Bancroft et al. |
| 6,342,359 | B1 | 1/2002 | Lee et al. |
| 6,399,397 | B1 | 6/2002 | Zarling et al. |
| 6,576,422 | B1 | 6/2003 | Weinstein et al. |
| 6,686,149 | B1 | 2/2004 | Sanchis et al. |
| 6,743,640 | B2 | 6/2004 | Whitten et al. |
| 6,995,256 | B1 | 2/2006 | Li et al. |
| 7,060,874 | B2 | 6/2006 | Wilkins |
| 7,115,301 | B2 | 10/2006 | Sheu et al. |
| 7,160,996 | B1 | 1/2007 | Cook |
| 7,223,906 | B2 | 5/2007 | Davis |
| 2002/0048822 | A1 | 4/2002 | Rittenburg et al. |
| 2002/0056147 | A1* | 5/2002 | Dau et al. ............ 800/8 |
| 2002/0187263 | A1 | 12/2002 | Sheu et al. |
| 2003/0142704 | A1 | 7/2003 | Lawandy |
| 2003/0142713 | A1 | 7/2003 | Lawandy |
| 2003/0162296 | A1 | 8/2003 | Lawandy |
| 2003/0177095 | A1 | 9/2003 | Zorab et al. |
| 2004/0063117 | A1 | 4/2004 | Rancien et al. |
| 2004/0166520 | A1 | 8/2004 | Connolly |
| 2004/0219287 | A1 | 11/2004 | Regan et al. |
| 2005/0059059 | A1 | 3/2005 | Liang |
| 2005/0214532 | A1 | 9/2005 | Kosak et al. |
| 2006/0017957 | A1 | 1/2006 | Degott et al. |
| 2006/0017959 | A1 | 1/2006 | Downer et al. |
| 2006/0117465 | A1 | 6/2006 | Willows et al. |
| 2006/0121181 | A1 | 6/2006 | Sleat et al. |
| 2006/0286569 | A1 | 12/2006 | Bar-Or et al. |
| 2007/0048761 | A1 | 3/2007 | Reep et al. |

FOREIGN PATENT DOCUMENTS

| | | |
|---|---|---|
| RU | 2170084 C1 | 10/2001 |
| WO | WO 87/06383 | 10/1987 |
| WO | WO 9014441 | 11/1990 |
| WO | WO 9502702 A1 | 1/1995 |
| WO | WO 9506248 | 3/1995 |
| WO | WO 97/45539 A1 | 12/1997 |
| WO | WO 98/06084 A1 | 2/1998 |
| WO | WO 9959011 | 11/1999 |
| WO | WO 00/55609 A2 | 9/2000 |
| WO | WO 01/25002 A1 | 4/2001 |
| WO | WO 0199063 A1 | 12/2001 |
| WO | WO 02057548 A1 | 7/2002 |
| WO | WO 02084617 A1 | 10/2002 |
| WO | WO 03/030129 A2 | 4/2003 |
| WO | WO 03080931 A1 | 10/2003 |
| WO | WO 2004/025562 A1 | 3/2004 |
| WO | WO 2004025562 A1 | 3/2004 |

OTHER PUBLICATIONS

Zuckermann, et al. "Efficient methods for attachment of thiol specific probes to the 3'-ends of synthetic oligodeoxyribonucleotides." Nucleic Acids Research, vol. 15, pp. 5305-5321 (1987). IRL Press Limited, Oxford, England.

Gupta, et al. "A general method for the synthesis of 3'-sulfhydryl and phosphate group containing oligonucleotides." Nucleic Acids Research, vol. 19, pp. 3019-3025 (1991). Oxford University Press, Oxford, England.

Agrawal & Tang. "Site-specific functionalization of oligodeoxynucleotides for non-radioactive labelling." Tetrahedon Letters, vol. 31, pp. 1543-1546 (1990). Pergamon Press, Great Britain.

Sproat, et al. The synthesis of protected 5'-mercapto-2', 5'-dicleoxyribonucleoside-3'-O-phosphoramidites; uses of 5'-mercapto-oligodeoxyribonucleotides.' Nucleic Acids Research, vol. 15, pp. 4837-4848 (1987). IRL Press Limited, Oxford, England.

Nelson, et al. "Bifunctional oligonucleotide probes synthesized using a novel CPG support are able to detect single base pair mutations." Nucleic Acids Research, vol. 17, pp. 7187-7194 (1989). IRL Press Limited, Oxford, England.

Heid, et al. "Real Time Quantitative PCR." Genome Research, vol. 6, pp. 986-994 (1996). Cold Spring Harbor Laboratory Press, Woodbury, New York.

Holland, et al. "Detection of specific polymerase chain reaction product by utilizing the 5' [to] 3' exonuclease activity of Thermus aquaticus DNA polymerase." Proceedings of the National Academy of Sciences, vol. 88, pp. 7276-7280 (1991). National Academy of Sciences, Washington, DC.

Lee, et al. "Allelic discrimination by nick-translation PCR with fluorogenic probes." Nucleic Acids Research, vol. 21, pp. 3761-3766 (1993). Oxford University Press, Oxford, England.

Nazarenko, et al. "A closed tube format for amplification and detection of DNA based on energy transfer." Nucleic Acids Research, vol. 25, pp. 2516-2521 (1997). Oxford University Press, Oxford, England.

Gibson, et al. "A Novel Method for Real Time Quantitative RT-PCR." Genome Research, vol. 6, pp. 995-1001 (1996). Cold Spring Harbor Laboratory Press, Woodbury, NY.

Tyagi & Kramer. "Molecular Beacons: Probes that Fluoresce upon Hybridization." Nature Biotechnology, vol. 14, pp. 303-308 (1996). Nature Publishing Group, New York.

Tyagi, et al. "Multicolor molecular beacons for allele discrimination." Nature Biotechnology, vol. 16, pp. 49-53 (1997). Nature Publishing Group, New York.

Whitcombe, et al. "Detection of PCR products using self-probing amplicons and fluorescence." Nature Biotechnology, vol. 17, pp. 804-807 (1999). Nature America, Inc., New York.

Van De Rijke, et al. "Up-converting phosphor reporters for nucleic acid microarrays." Nature Biotechnology, vol. 19, pp. 273-276 (2001). Nature Publishing Group, New York.

Corstjens, et al. "Infrared up-converting phosphors for bioassays," IEE Proceedings—Nanobiotechnology, vol. 152, pp. 64-72 (2005). Institution of Engineering and Technology, London.

Versalift, "Market Growth: the evolution of the aerial lift industry." Oct. 1, 2002. Accessed on web Nov. 10, 2006.

Schultz et al., "Archived or directly swabbed latent fingerprints as a DNA source for STR typing." Forensic Science International 127 (2002) 128-130.

Hussein et al. "Molecular Characterization of Cotton Genotypes Using PCR-based Markers." Journal of Applied Sciences Research 3 (10) 1156-1169 (2007).

Jiang et al. "Polyploid formation created unique avenues for response to selection in Gossypium (cotton)," Proceedings of the National Academy of Sciences, USA. vol. 95 pp. 4419-4424, Apr. 1998.

Lee et al. "The complete chloroplast genome sequence of Gossyplum hirsuturn organization and phylogenetic relationships to other angiosperms." BMC Genomics 7:61, Mar. 2006.

* cited by examiner

SEQUENCE LISTING

<160> NUMBER OF SEQ ID NOS: 2

<210> SEQ ID NO 1
<211> LENGTH: 24
<212> TYPE: DNA
<213> ORGANISM: Unknown
<220> FEATURE:
<223> OTHER INFORMATION: primer  artificial sequence

<400> SEQUENCE: 1
cgccagggtt tcccagtca cgac                                              24

```
<210> SEQ ID NO 2
<211> LENGTH: 17
<212> TYPE: DNA
<213> ORGANISM: Unknown
<220> FEATURE:
<223> OTHER INFORMATION: primer  artifical sequence

<400> SEQUENCE: 2
caggaaacag ctatgac                                                    17
```

SYSTEM AND METHOD FOR AUTHENTICATING TABLETS

CROSS REFERENCE

This application is a continuation-in-part of patent application Ser. No. 11/437,265 having a filing date of May 19, 2006 that is related to provisional patent application 60/682,976 filed on May 20, 2005; this application is also a continuation-in-part of patent application Ser. No. 10/825,968 having a filing date of Apr. 15, 2004 that is related to provisional patent application 60/463,215 filed on Apr. 16, 2003; this application is also related to provisional patent application 60/874,425 having a filing date of Dec. 12, 2006; this application is also related to provisional patent application 60/877,875 having a filing date of Dec. 29, 2006; this application is also related to provisional patent application 60/877,869 having a filing date of Dec. 29, 2006; each of the patent applications being hereby incorporated by reference including patent application Ser. No. 11/954,009 now issued as U.S. Pat. No. 8,124,333; Ser. No. 11/954,030 now issued as U.S. Pat. No. 8,372,648; Ser. Nos. 11/954,038, 11/954,044 and 11/954,051; each of which were co-filed with the present application on Dec. 11, 2007.

FIELD

This invention relates to a system and method for authenticating one or more tablets. More particularly, the invention is related to a method for detecting and verifying the authenticity of tablets.

BACKGROUND

With the dawn of modern technical advances comes the ability to duplicate, change, alter and distribute just about anything. The Law enforcement organizations have called counterfeiting the crime of the 21$^{st}$ century. Product counterfeiting is a serious and growing threat. Measures to defend against counterfeiters are being taken by many corporations, but they have not developed comprehensive, systematic, and cost-effective solutions to preventing counterfeiting.

Due to advancing counterfeiting techniques, traditional anti-counterfeit technologies are becoming obsolete. Additionally, governments and corporations that have invested a great deal of resources in fighting counterfeiting have experienced little success. Furthermore, law enforcement agencies that are burdened with efforts to combat violent crimes have insufficient resources to fight the "victimless" counterfeiting crime. For example, a company owning a famous brand name may have spent years developing and promoting the superior qualities of its goods to establish good will of the public and may be unable to stop a counterfeiter or a newcomer company product inferior quality goods.

Counterfeiting also extends to medical and pharmaceutical areas where counterfeiting can pose a serious threat and danger to public health. For example, goods such as oral pharmaceuticals encapsulated in tablets may be easily counterfeited. Counterfeiting of this nature is particular adverse to the interests of original manufacturers of the drugs because this negatively impacts the sales of their products, but this also allows the wide and unsafe dissemination of dubious drugs. Consequently, both the public and the manufacturer face serious health and medical consequences and liability vis a vis the public because consumers may be sold counterfeit gray goods such as counterfeit drugs unbeknownst to them.

For example, one such difficulty lies in determining the origin of the drugs, particularly if the drugs themselves are not marked in such as way as to unequivocally determine their authenticity. This has often been the case with tablets. A problem is that although a package containing tablets may include a source designation code and other identifying brand or laboratory indicia, the tablet itself is not assigned such a code and may therefore be easily repackaged to hide its channel of distribution. Further, the absence of such a code or marking fails to assist in the identification of the distributor licensee that was responsible. Often tablet containers and packaging are properly marked and sealed so that the manufacturing source can be identified by some ID number. Since the container is sealed, one would expect that the tablets inside the container, for example, match the lot number on the container. Regrettably, as the cost of medication rises, the temptation grows for domestic and international manufacturers or suppliers to substitute some or all of the tablets of the container with a cheaper generic version or worse, inferior quality or counterfeit drugs, then seal the container, and pass it off as containing the tablets from the original name brand. It is likely that the consumer will not suspect the switch, although some may notice that the medication is less effective than expected. Regardless, the business profits handsomely. The manufacturer of the brand name product, however, in effect loses a sale and, worse, loses some of its good will as the consumer wrongfully blames the brand name manufacturer for the poor quality over which the manufacturer had no control. If the consumer suffers medically from the switched medication, the integrity of the brand name is damaged, not to mention the serious legal and product liability the manufacturer faces. In addition, the consumer does not get the brand name product for which he or she paid a premium. One reason this problem arises is because the consumer has no way of checking whether the tablets in the container are the proper tablets made by the labeled manufacturer.

Thus, many approaches have been proposed for authenticating drugs and solid pharmaceutical goods, but none of these have proven entirely satisfactory. In particular, such proposed approaches do not provide an effective foolproof anti-piracy deterrent because many can be tampered with. For example, applying a bar code on the surface of a tablet can be easily tampered with. Such micro bar codes and administration of bar indicia on tablets, normal printing procedures such as roller rotation methods, ink-jet printing of tablets, are well known but not foolproof against forgeries and can be labor intensive to implement due to different porosity of pharmaceutical drugs, different quality of active ingredients of a tablet, the different thickness, absorption and smoothness of the tablets, the non-planar small surface of the various types of different tablets, etc. This means that all these factors affect and influence the quality of the authentication and marking.

Therefore, these previously known approaches do not provide adequate authentication and can often be defeated by clever tampering, copying, spoofing, or other advanced counterfeiting techniques. With all these facts in mind, the realization of a simple method for labeling or printing pharmaceutical drugs using high quality standards and a simple method for verification seems to be out of reach.

SUMMARY

This invention relates to methods for authenticating pharmaceutical tablets and pills. The invention utilizes compositions which link biomolecules to visual or machine-detectable reporters. The methods of authentication comprise placing, associating, or integrating an optical reporter taggant with the tablet or other item of interest. The optical reporters can be easily detected by using a high energy light source for excitation, with the location of labeled biomolecules identified by the presence of an optical reporter. The location and emission wavelength of the optical reporters provides a first level of security or authentication of the tagged item of interest. After the location of the optical reporters and associated biomolecules on the item has been determined, the biomolecules may be characterized and identified to further increase the level of security and/or authenticity of the item. When the biomolecule attached to the optical reporter is a DNA molecule, PCR or sequence analysis techniques can be utilized to further authenticate the item.

In one embodiment the invention provides an authentication method for authenticating a tablet, the method comprising, applying a particular nucleic acid material to the tablet, the nucleic acid material associated with a particular sequence of nucleic acid bases; detecting the particular nucleic acid material, collecting a sample of the nucleic acid material from the tablet, and verifying said tablet is genuine by detecting said particular nucleic acid material in said tablet. In some embodiments, verifying the presence of the nucleic acid material comprises performing a polymerase chain reaction (PCR).

In most embodiments, the particular nucleic acid material is deoxyribonucleic acid (DNA). In other embodiments, the particular nucleic acid material is ribonucleic acid (RNA).

In certain embodiments, the applying the tablet with a particular nucleic acid material associated with a particular sequence of nucleic acid bases comprises performing the marking throughout the entire surface of the tablet.

In other embodiments the applying the tablet with a particular nucleic acid material associated with a particular sequence of nucleic acid bases comprises performing the marking in a specific area on the surface of the tablet.

In some embodiments, the marking further comprises a form of human recognizable symbolic icon.

In other embodiments the marking of the tablet, comprises a form of machine readable code, providing tablet identification.

In some embodiments, the method further comprises, applying a particular nucleic acid material associated with a particular sequence of nucleic acid bases on a package associated with the tablet to verify authenticity of the source and distributor of the tablet prior to consumption of the tablet by a user.

In certain embodiments, the tablet to be authenticated is selected from the group consisting of a caplet, a gel-cap, a pellet, a gum-piece, a capsule, an edible item that is biocompatible that contains any consumable herb, chemical, mineral, vitamin, plant or animal product, or placebo.

In certain embodiments, the method for authenticating a tablet comprises the steps of, providing an optical reporter marker, the optical reporter marker having at least one light emitting upconverting phosphor particle linked to at least one nucleic acid material, the nucleic acid material having an identifiable portion, introducing the optical reporter marker to the tablet or packaging for the tablet of interest, then detecting the optical reporter marker associated with the tablet with a light source, obtaining a sample of the optical reporter marker from the tablet or tablet packaging of interest for analysis; followed by analyzing the collected sample to detect the presence of the identifiable portion of the nucleic acid material linked to the upconverting phosphor particle.

In some embodiments, the methods for authenticating drugs or tablets involve marking primary and/or secondary packaging configured with the tablet that utilize compositions which link biomolecules to visual or machine-detectable reporters. The methods of authentication comprise placing, associating, or integrating an optical reporter taggant with the tablet packaging. The optical reporters can be easily detected by using a high energy light source for excitation, with the location of labeled biomolecules identified by the presence of an optical reporter. The location and emission wavelength of the optical reporters provides a first level of security or authentication of the tagged tablet packaging. After the location of the optical reporters and associated biomolecules on the tablet packaging has been determined, the biomolecules may be characterized and identified to further increase the level of security and/or authenticity of the tablet. When the biomolecule attached to the optical reporter is a DNA molecule, PCR or sequence analysis techniques can be utilized to further authenticate the drug of interest.

It should be understood that "authenticating a tablet" includes directly labeling the tablet or during with the DNA marker and also includes indirectly labeling a tablet by labeling the primary or secondary packaging associated with the tablet to be authenticate with a DNA marker.

In many embodiments of the method for authenticating a drug or tablet comprises the steps of;

providing an optical reporter marker, the optical reporter marker having at least one light emitting upconverting phosphor particle linked to at least one nucleic acid taggant, the nucleic acid taggant having an identifiable portion, introducing the optical reporter marker to the tablet and/or to the packaging associated with the tablet, detecting the optical reporter marker associated with the tablet with a light source, obtaining or collecting a sample of the optical reporter marker from the tablet or tablet packaging for analysis; and analyzing the collected sample to detect the presence of the identifiable portion of the nucleic acid taggant linked to the upconverting phosphor particle. In many embodiments the analyzing of the collected sample comprises determining the DNA sequence of the nucleic acid taggant, and comparing the determined DNA sequence with a known or reference DNA sequence.

In some embodiments, the optical reporter marker provided in the methods of the invention comprises a composition of the formula I:

$$(cOpR)\text{-}[L\text{-}(NA)]_m \qquad \qquad I$$

wherein: m is an integer greater than 1, (cOpR) is a coated optical reporter particle, (NA) is a nucleic acid oligomer of detectable sequence and L is a linking group covalently bound to the coated optical reporter particle and to the nucleic acid oligomer.

The (cOpR) of the composition may comprise an upconverting phosphor (UCP) material coated with silica. Where the compositions are coated with silica, the silica comprises at least one Si—O bond.

The (NA) of the composition maybe a single or double stranded DNA molecule having a length of between about 40 base pairs and about 1000 base pairs.

The linker L of the composition may comprise an alkylene moiety having a first end covalently bound to the coated optical reporter particle and a second end covalently bound to the nucleic acid oligomer.

Where the composition utilized in the methods of the invention comprises a (UCP), in certain embodiments, the (UCP) is an upconverting phosphor particle of the formula:

$$Y_xYb_yEr_zO_2S;\ or$$

$$Na(Y_xYb_yEr_z)F_4;$$

wherein:
x is from about 0.6 to about 0.95;
y is from about 0.05 to about 0.35; and
z is from about 0.1 to about 0.001.
In other embodiments, the linker L may be of the formula:

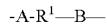

where $R^1$ is $C_{2-8}$alkylene, -A- is a group covalently bonded to the surface of the coated optical reporter and —B— is a group covalently bonded to the 3' or 5' end of the nucleic acid oligomer.

In other embodiments, a composition used in the methods for authenticating a sports garment of the invention has the formula:

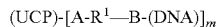

where m is an integer greater than 1; UCP is an upconverting phosphor particle; DNA is a single or double stranded deoxyribonucleic acid oligomer; $R^1$ is $C_{2-8}$alkylene; -A- is a group capable of covalently bonding to the surface of the upconverting phosphor particle and —B— is a group capable of bonding to the 3' or 5' end of the deoxyribonucleic acid oligomer.

All patents and publications identified herein are incorporated herein by reference in their entirety.

DESCRIPTION

Figure 1:
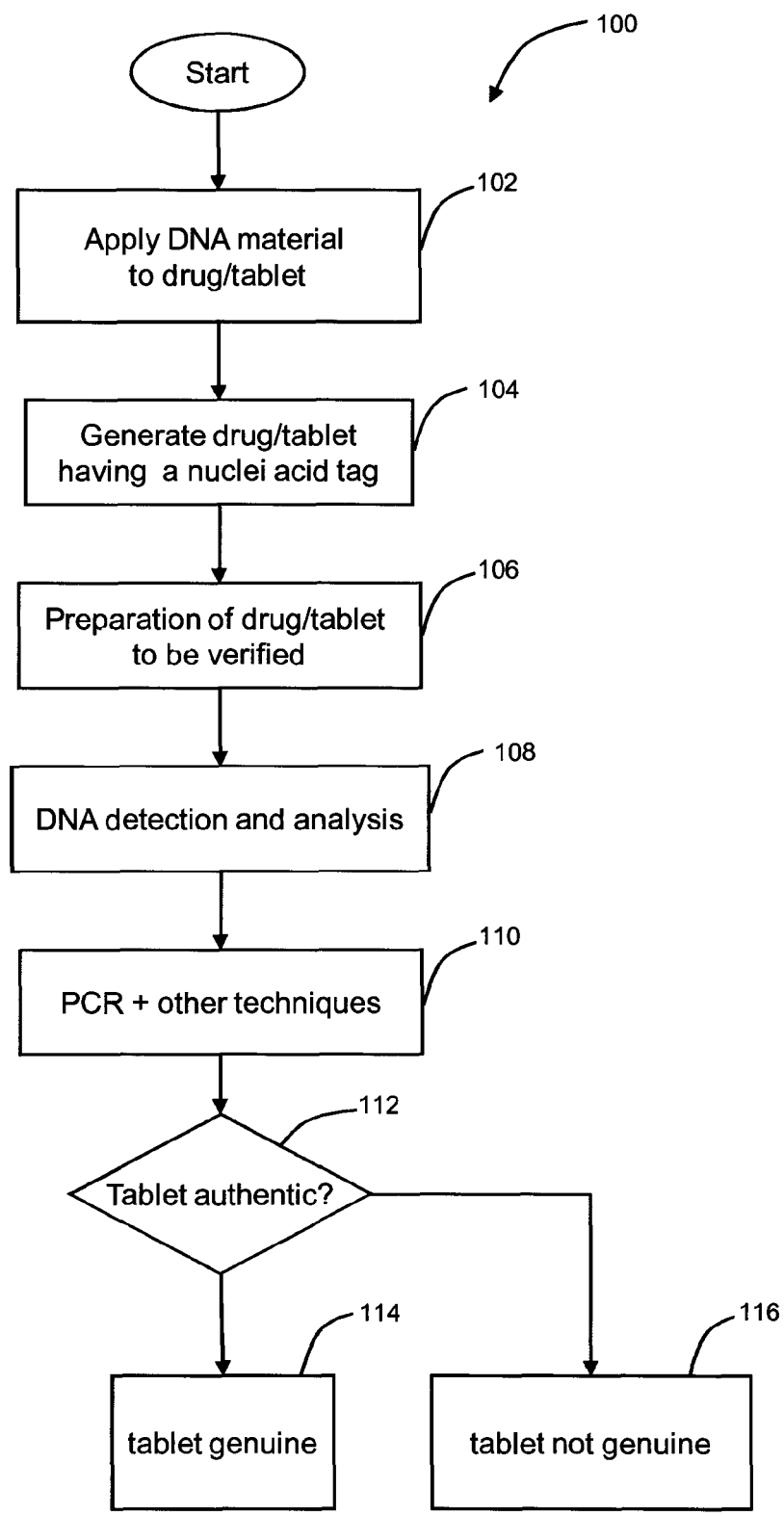
FIG. 1 is a flow chart of one embodiment of the methods of the invention.

Before the present methods for authenticating products are described, it is to be understood that this invention is not limited to particular product described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a taggant" includes a plurality of such taggants and reference to "the primer" includes reference to one or more primers and equivalents thereof known to those skilled in the art, and so forth.

If any publications are discussed here, they are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula —R'—R"—R"" where R' is alkylene, R" is —SO$_2$— and R"" is alkyl as defined herein.

"Amino means a moiety of the formula —NR—R' wherein R and R' each independently is hydrogen or alkyl.

"Alkylsulfanyl" means a moiety of the formula —SR wherein R is alkyl as defined herein.

"Urea" or means a group of the formula —NR'—C(O)—NR"R"" wherein R', R" and R"" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R"" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

The term "emitting reporter" means a chemical substituent or material that produces, under appropriate excitation conditions, a detectable optical signal. The optical signal produced by an emitting reporter is typically electromagnetic radiation in the near-infrared, visible, or ultraviolet portions of the spectrum. The emitting reporters of the invention are generally up-converting reporters, but can also be for example, fluorescent and calorimetric substituents.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via a temperature cycling techniques in the presence of a nucleotide polymerase, preferably a DNA polymerase. This includes but is not limited to real-time PCR technology, reverse transcriptase-PCR, and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" or "nucleotide" refer to single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like. The term nucleotide means The term "linker" means a compound or a composition which covalently links a biomolecule to the surface of a coated emitting reporter. For example, but not limited to a silyinated coated upconverting phosphor particle linked to a DNA molecule.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

A "Nucleic acid tag" is a nucleic acid oligomer or fragment used to identify or authenticate a particular product. Nucleic acid tag and nucleic acid taggant are interchangeable throughout the specification.

The term "DNA taggant" means a nucleic acid tag which comprises deoxy nucleotides. A DNA taggant maybe double stranded or single stranded, cDNA, STR (short tandem repeats) and the like. The DNA taggant may also comprise modification to one or more nucleotides which aid in the identification or detection of the DNA taggant.

The term "DNA marker compound" means a marker compound utilized to identify or authenticate a particular product which comprises a specific DNA oligomer which is used to authenticate the particular product.

The terms "Pharmaceuticals" or "Pills" or "Drugs" or "Vitamins" or "Supplements" are used interchangeably throughout this patent application. These terms refer to chemical compounds that are consumed as tablets, caplets, gel-caps, capsules or other such tablets that contain one or more chemical compounds. Tablets come in a variety of shapes, sizes and colors to help distinguish them from one another because tablets from different suppliers contain the same medication, and it makes sense for safety reasons to differentiate the configuration to avoid the potential for mix-up in the event of switching between brands. Such a mix-up may lead to severe health risks and could be lethal.

The terms "Pill packaging" or "Tablet Packaging" refer to containers, from single pill containers to containers that contain thousand of pills.

The terms "those defined above" and "those defined herein" when referring to a variable incorporates by reference the broad definition of the variable as well as preferred, more preferred and most preferred definitions, if any.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.5. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. Vv A method for labeling pharmaceuticals and readily verifying their authenticity as genuine by combining a drug with a specified nucleic acid tag and then detecting the nucleic acid tag in the drug in an effective manner is described. In the case of pills and drugs, either in solid or liquid form, the drug (i.e. pills, gel capsules, etc.) may have the nucleic acid tag incorporated completely throughout the pill. If the product is a prescription drug in tablet form, the nucleic acid marker compound maybe in the form of a solid which can be introduced into the product (drug) during the compression of the drug into a tablet.

FIG. 1 shows a flow chart of the general process 100 of introducing a nucleic acid tag to a tablet and being able to detect the nucleic acid tag or marker incorporated therein. Introducing the nucleic acid tag to a tablet may comprise direct labeling of the drug with the nucleic acid tag or introducing the nucleic acid tag to a primary or secondary packaging associated with the tablet. The process comprises providing at least one specific nucleic acid fragment as an authentication tag or marker for a product in step 102. The nucleic acid marker maybe DNA, cDNA, or other DNA material, or any other nucleic acid fragment comprising nucleic acids or nucleic acid derivatives. The marker may be a nucleic acid fragment that is single stranded or preferably, double stranded and may vary in length, depending on the product to be labeled as well as the detection technique utilized in the nucleic acid marker detection process.

The nucleic acid marker may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid marker/tag usually ranges between about 100 to about 10 kilo bases, more usually about 500 bases to about 6 kb, and about 1 kb to about 3 kb in length. The form of the DNA may be linear or circular with sizes ranges from a few bases (5 bases) to genomic DNA (1M to 30B bases).

When the nucleic acid marker is configured to an optical reporter, the size of the nucleic acid of known sequence maybe considerably smaller than the sizes mentioned above. The length of the nucleic acid tag, when associated with an optical reporter material, usually ranges between about 50 to about 1 kilo bases, more usually about 100 bases to about 800 bases, and preferably 150 bases to about 500 bases in length.

There are several possible methods of DNA tagging. For example, the DNA may be combined with: excipients such as, hydroxypropylcellulose, hydroxyethylcellulose, sodium carboxymethylcellulose, and ethycellulose; binder such as microcrystalline cellulose, lactose powder, sucrose powder, and cassava flour; disintegrant such as starch; lubricant such as stearic acid (stearin) and magnesium stearate; or any combination thereof.

The nucleic acid taggant may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

For exemplary purposes, the nucleic acid concentration may vary from pico grams ($1 \times 10^{-12}$ gram) to micro grams ($1 \times 10^{-9}$ gram). In some embodiments, the DNA concentration may range from 1 ppb (parts per billion) to 500,000 ppm.

In certain embodiments for the methods of the invention, the nucleic acid marker is derived from DNA extracted from a specific plant source and rendered non-functional with scrambled sequences. The DNA may also be specifically digested and ligated to generate artificial nucleic acid sequences which are unique to the world. The digestion and ligation of the extracted DNA is completed by standard restriction digestion and ligase techniques known to those skilled in the art of molecular biology. Once the modified DNA taggant has been produced, the taggant is encapsulated into materials for protection against UV and degradation. The DNA encapsulant materials are generally of plant origin.

The marker compound maybe produced as a solid or liquid, water or oil based, a suspension, an aggregate and the like. In certain embodiments, the marker compound is configured to protect the nucleic acid fragment from UV and other degradation factors that may degrade the nucleic acid taggant over-time, while the nucleic acid acts as an authentication tag for the drug. In some embodiments, when the taggant is DNA, the nucleic acid tag may be encapsulated and suspended in a solvent solution (aqueous or organic solvent solution) producing a "stock" DNA taggant solution at a specified concentration. This stock DNA solution can then easily be added to the marker compound mixture at an appropriate concentration for the type of product to be authenticated. In certain instances, the DNA taggant maybe mixed with other components of the marker compound without any prior encapsulation. Several processes such as nucleic acid fragment encapsulation and other techniques utilized for protecting nucleotides, and in particular, DNA from degradation, are well known in the art.

In certain embodiments, the marker compound mixture is able to camouflage or "hide" the specified nucleic acid tag with extraneous and nonspecific nucleic acid oligomers/fragments, thus making it difficult for unauthorized individuals, such as forgers to identify the sequence of the nucleic acid tag. The marker compound comprises a specified dsDNA taggant from a known source (i.e. mammal, invertebrate, plant and the like) along with genomic DNA from the corresponding or similar DNA source. The amount of the DNA taggant found in a marker compound varies depending on the particular product to be authenticated, the duration the taggant needs to be viable (e.g. 1 day, 1 month, 1 year, multiple years) prior to authentication, expected environmental exposure, the detection method to be utilized, etc.

After the nucleic acid fragment/marker compound with a known nucleic acid sequence has been manufactured, for direct tablet labeling the nucleic acid tag is integrated into the material(s) utilized in the preparation of the tablet, and the method further comprises generating a pill/tablet comprising the DNA fragment marker or tag in event 104. In the embodiment illustrated in FIG. 1, the nucleic acid marker is represented throughout the complete pill. The formation of the tablet is completed using methods known to those skilled in the art of tablet formation. The NA marker is mixed with the drug, as well as inert substances utilized in the formation of the tablet.

Figure 3:
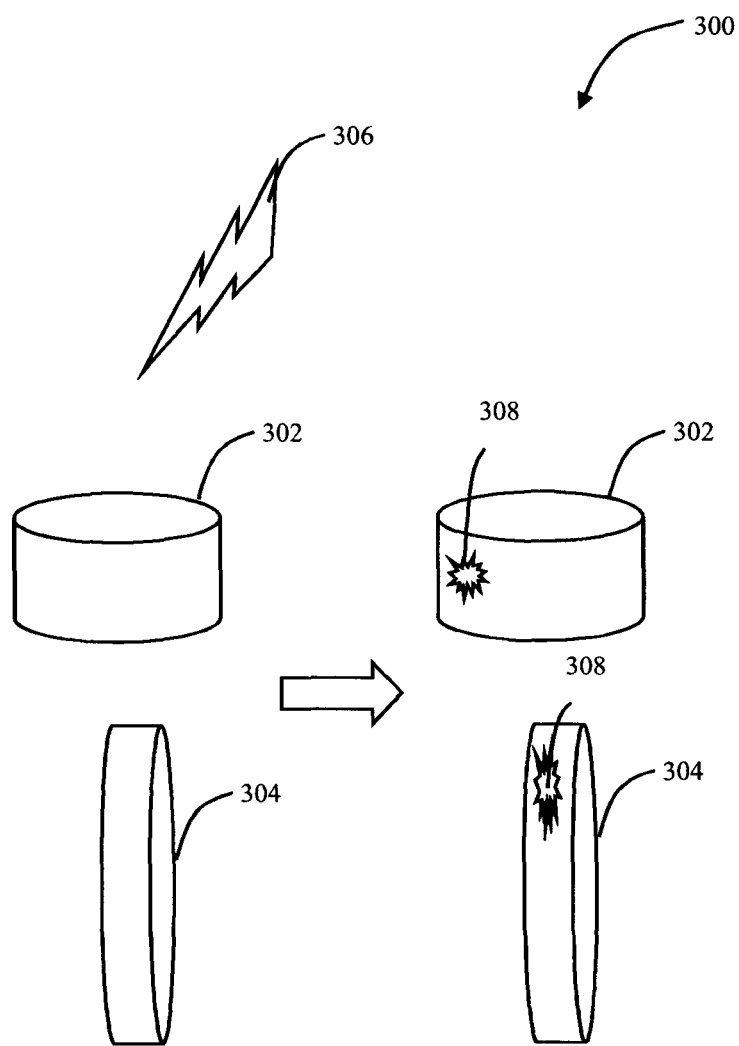
FIG. 3 is an illustrative diagram of a labeling process of a tablet in accordance with one of the embodiments of the present invention.
Figure 4:
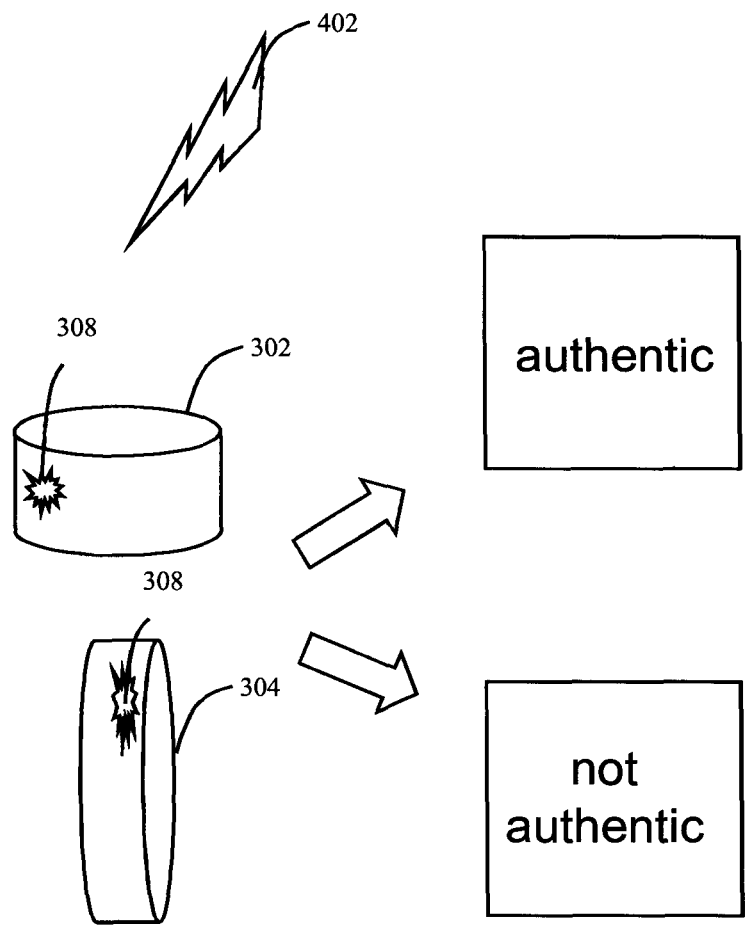
FIG. 4 is an illustrative diagram of a tablet verification process according one of the embodiments of the present invention.

In other embodiments, the tablet is formed prior to tagging the drug with the NA marker and a specified amount of the nucleic acid marker is placed on at least one portion of the surface of the tablet as shown in FIGS. 3 and 4. The NA marker maybe placed on the surface of the tablet in a liquid or solid form. Many tablets comprise an outer coating which aids in swallowing the tablet. The NA marker can be mixed with the coating material and applied to the tablet or it be applied in addition to the coating. The NA marker may also be applied to the tablet in a certain and distinct configuration, such as indicia related to the drug within the tablet.

In certain embodiments, the tablet is authenticated by labeling a primary and/or secondary packaging associated with the tablet. After the nucleic acid tag has been manufactured, the nucleic acid tag is integrated into a mixture such as an ink or paint which can be placed on a predetermined location of the tablet packaging. The primary or secondary packaging may be labeled with the nucleic acid tag prior to or after being configured with the tablet(s) of interest. Labeling the packaging, in certain embodiments, maybe preferable to labeling the tablet directly due to federal drug regulations which may prevent the labeling of the drug with a nucleic acid tag. Also a plurality of tablets can be authenticated simultaneously by authenticating the primary or secondary packaging of the drug of interest.

In general, when the taggant is dsDNA, PCR is the technique for taggant detection as described in event 110 below. The copy number of DNA taggant in a predetermined sample size of marker compound used for authentication is about 3 copies to about 100,000 copies, more usually about 10 copies to about 50,000 copies, and even more usually about 100 copies to about 10,000 copies of DNA taggant. The concentration of NA taggant within the tablet or a tablet coating may be varied as required depending upon particular embodiments of the invention. PCR can effectively detect extremely small amounts of DNA taggant and skilled persons can easily formulate DNA-labeled pills or drugs using the invention.

The embodiment of the method of authenticating and verifying a pill depicted in FIG. 1 further comprises preparing the pill to be verified as in step 106. In step 108, a sample is collected of the particular pill of interest for verification, i.e., DNA analysis on whether the pill contains the nucleotide tag. For example, when the item being prepared is a solid tablet, a portion of the tablet containing the NA-tag may be cut, scraped, abraded, or otherwise removed from the tablet for analysis. Preparation of the tablet may require solvent treatment prior to removing a sample for verification. Preparation of the pill may also occur without further purification, but usually, some extraction, isolation or purification of the nucleic acid tag obtained in the sample is required. Details on the extraction, concentration and purification techniques useful for the methods of the invention are described more fully below and also in the examples.

In certain embodiments the placement or position of the NA marker on the tablet maybe located by the detection of materials or compounds configured to or associated with the NA fragment in the NA marker. Event 108 provides for such detection of the DNA marker. In many embodiments the DNA marker may be bound or coupled to, or otherwise associated with, a chemically or optically detectable label. Detection of DNA-labeled portions of the tablet may be carried out by optically detecting fluorescent dyes or upconverting phosphor particles which can be detected easily by UV and/or IR portable light sources. Thus, for example, a tablet could be examined with a UV or IR light source to find a particular region or regions of the tablet that contain a particular fluorescent marker. In this manner, only a small portion of the tablet (as identified by the fluorescent dye or particles) needs to be sampled for DNA. The materials or compounds utilized for locating the position of the NA marker on a tablet maybe coated with functional groups which can covalently bind to the NA fragment(s) of the NA marker, as described below. Event 108 may be carried out prior to event 106.

In general, analyzing the pill for the presence of DNA in event 110, comprises providing a "detection molecule" configured to the nucleic acid tag. A detection molecule includes but is not limited to a nucleic acid probe and/or primer set which is complementary to the sequence of the nucleic acid taggant, or a dye label or color producing molecule configured to bind and adhere to the nucleic acid taggant.

DNA may be extracted from tablet or capsule and then subjected to PCR amplification using specific primers where amplicons are analyzed with gel electrophoresis, capillary electrophoresis; real time-PCR detection techniques. When the detection of the nucleic acid taggant comprises amplifying the nucleic acid taggant using PCR, the detection molecule(s) are primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or quantitative authentication results.

With the use of real time PCR, results from the analysis of the pill sample can be completed within 30 minutes to 2 hours, including extracting or purifying the nucleic acid taggant from the collected sample. Various embodiments utilize a wide range of detection methods besides for PCR and real time PCR, such as fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection.

The results of the analysis of the pill are reviewed to determine if the specific nucleic acid taggant was detected in the sample. If so, in step 112, the authentication of whether the pill is genuine or not can be verified. If the nucleic acid taggant is not found or detected in the pill of interest, the conclusion from the analysis is the that pill is not authentic or has been tampered with as in step 116. If the nucleic acid taggant is detected in the pill, then the pill is verified as being authentic as in step 114.

In some embodiments, the quantity or concentration of the nucleic acid taggant within a collected sample can be determined and compared to the initial amount of nucleic acid taggant placed in the product to allow for the detection of fraud caused by diluting the product with inferior products by forgers. In general, quantitative detection methods comprise providing an internal or external control to evaluate the efficiency of detection from one sample/analysis to the next. The efficiency of detection may be affected by many parameters such as, probe hybridization conditions, molecules or substances in the product which may interfere with detection, and/or primer integrity, enzyme quality, temperature variations for detection methods utilizing PCR. By providing a control, in the detection methods, any variable conditions can be normalized to obtain an accurate final concentration of the nucleic acid tag in the product.

Incorporation of Functional Groups

In certain embodiments, the nucleic acid tag is labeled with at least one compound or "detection molecule" prior to being incorporated into the specified product to aid in the extraction and/or detection of the nucleic acid marker from the product after being placed in a supply chain. A detection molecule is a molecule or compound with at least one functionality. For example, fluorescent molecules may be configured to the nucleic acid marker for certain detection methods which are described in detail below.

In certain preferred aspects, suitable dyes include, but are not limited to, coumarin dyes, xanthene dyes, resorufins, cyanine dyes, difluoroboradiazaindacene dyes (BODIPY), ALEXA dyes, indoles, bimanes, isoindoles, dansyl dyes, naphthalimides, phthalimides, xanthenes, lanthanide dyes, rhodamines and fluoresceins. In other embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the authentication process described herein. In certain embodiments, suitable dyes include, but are not limited to, fluorescein, 5-carboxyfluorescein (FAM), rhodamine, 5-(2'-aminoethyl)aminonapthalene-1-sulfonic acid (EDANS), anthranilamide, coumarin, terbium chelate derivatives, Reactive Red 4, BODIPY dyes and cyanine dyes.

There are many linking moieties and methodologies for attaching fluorophore or visible dye moieties to nucleotides, as exemplified by the following references: Eckstein, editor, *Oligonucleotides and Analogues: A Practical Approach* (IRL Press, Oxford, 1991); Zuckerman et al., *Nucleic Acids Research*, 15: 5305-5321 (1987) (3' thiol group on oligonucleotide); Sharma et al., *Nucleic Acids Research*, 19: 3019 (1991) (3' sulfhydryl); Giusti et al., *PCR Methods and Applications*, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); AP3 Labeling Technology (U.S. Pat. Nos. 5,047,519 and 5,151,507, assigned to E.I. DuPont de Nemours & Co); Agrawal et al, *Tetrahedron Letters*, 31: 1543-1546 (1990) (attachment via phosphoramidate linkages); Sproat et al., *Nucleic Acids Research*, 15: 4837 (1987) (5' mercapto group); Nelson et al, *Nucleic Acids Research*, 17: 7187-7194 (1989) (3' amino group); and the like.

In other embodiments, the complementary nucleic acid probe is labeled with at least one compound or molecule with functionality to aid in the detection of the nucleic acid tag/marker. The techniques and dyes utilized in labeling the nucleic acid tag or the complementary probe are the same due to the nucleic acid nature of the tag and probe.

The detection molecules of the invention can be incorporated into probe motifs, such as Taqman probes (Held et al., Genome Res. 6: 986-994 (1996), Holland et al., Proc. Nat. Acad. Sci. USA 88: 7276-7280 (1991), Lee et al., Nucleic Acids Res. 21: 3761-3766 (1993)), molecular beacons; Tyagi et al., Nature Biotechnol., 16:49-53 (1998), U.S. Pat. No. 5,989,823, issued Nov. 23, 1999)) scorpion probes (Whitcomb et al., Nature Biotechnology 17: 804-807 (1999)), sunrise probes (Nazarenko et al., Nucleic Acids Res. 25: 2516-2521 (1997)), conformationally assisted probes (Cook, R., copending and commonly assigned U.S. Provisional Application No. 60/138,376, filed Jun. 9, 1999), peptide nucleic acid (PNA)-based light up probes (Kubista et al., WO 97/45539, December 1997), double-strand specific DNA dyes (Higuchi et al, Bio/Technology 10: 413-417 (1992), Wittwer et al, Bio/Techniques 22: 130-138 (1997)) and the like. These and other probe motifs with which the present detection molecules can be used are reviewed in Nonisotopic DNA Probe Techniques, Academic Press, Inc. 1992.

In other embodiments, the molecular beacon system is utilized to detect and quantify the nucleic acid tag from the product of interest. "Molecular beacons" are hairpin-shaped nucleic acid detection probes that undergo a conformational transition when they bind to their target that enables the molecular beacons to be detected. In general, the loop portion of a molecular beacon is a probe nucleic acid sequence which is complementary to the nucleic acid marker. The stem portion of the molecular beacon is formed by the annealing of arm sequences of the molecular beacon that are present on either side of the probe sequence. A functional group such as a fluorophore (e.g. coumarin, EDNAS, fluorescein, lucifer yellow, tetramethylrhodamine, texas red and the like) is covalently attached to the end of one arm and a quencher molecule such as a nonfluorescent quencher (e.g. DABCYL) is covalently attaches to the end of the other arm. When there is no target (nucleic acid tag) present, the stem of the molecular beacon keeps the functional group quenched due to its close proximity to the quencher molecule. However, when the molecular beacon binds to their specified target, a conformational change occurs to the molecular beacon such that the stem and loop structure cannot be formed, thus increasing the distance between the functional group and the quencher which enables the presence of the target to be detected. When the functional group is a fluorophore, the binding of the molecular beacon to the nucleic acid tag is detected by fluorescence spectroscopy.

In certain embodiments, a plurality of nucleic acid tags with varying sequences are used in labeling a particular product. The different nucleic acid tags can be detected quantitatively by a plurality of molecular beacons, each with a different colored fluorophore and with a unique probe sequence complementary to at least one of the plurality of nucleic acid tags. Being able to quantitate the various fluorphores (i.e. various nucleic acid tags) provides a higher level of authentication and security. It should be noted, that the other functional groups described above useful in labeling nucleic acid probes can also be utilized in molecular beacons for the present invention.

In other embodiments, the methods for authenticating a tablet comprises labeling the tablet with an optical reporter marker linked to a nucleic acid tag, detecting the optical reporter, and then characterizing or verifying the nucleic acid taggant associated with the tablet in an effective manner, by nucleic acid sequencing, genotyping or like techniques. This embodiment allows for verification of tagged or marked tablets in a manner that's helps prevent forgers counterfeit producers from substituting false or counterfeit drugs in place of authentic items.

Figure 2:
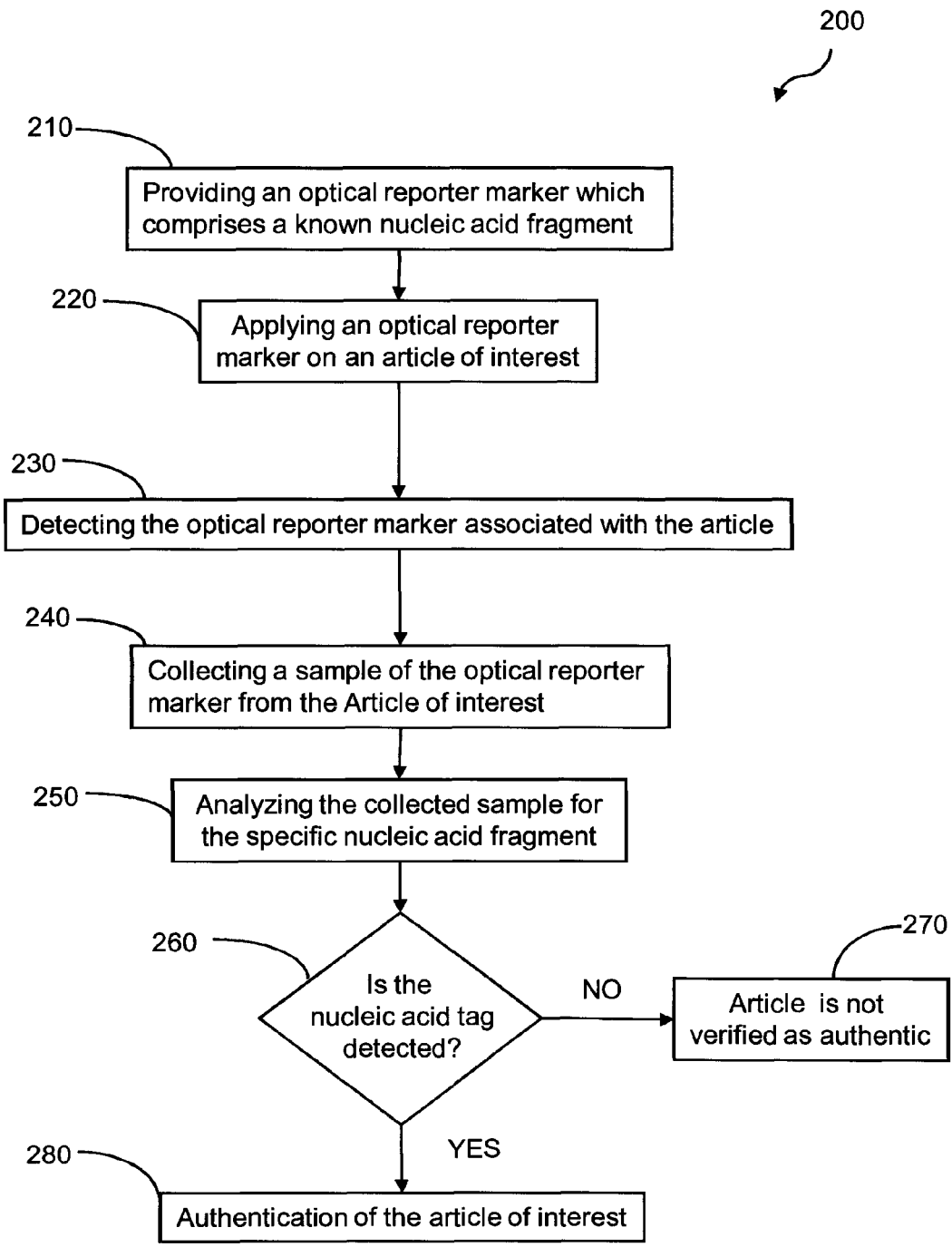
FIG. 2 is a flow chart of one embodiment of the methods for authenticating an item in accordance with the invention.

FIG. 2 is a flow chart illustrating generally a method 200 for authenticating a tablet or tablet packaging with a nucleic acid-linked optical reporter marker in accordance with the invention. The method 200 comprises, at event 210, providing an optical reporter marker having a nucleic acid taggant linked to an optical reporter particle, the nucleic acid taggant having a known portion of its sequence identifiable or sequenceable.

The optical reporter particle of event 210 is a light emitting optical reporter and in most embodiments is an upconverting phosphor particle (UCP). In certain embodiments the upconverting phosphor particle UCP is coated with a silylination composition which is configured to covalently link to the nucleic acid taggant. Specific UCPs usable with the invention are described further below.

The nucleic acid (NA) taggant of event 210 may be DNA, cDNA, or any other nucleic acid fragment comprising nucleic acids or nucleic acid derivatives. The NA maybe a nucleic acid fragment that is single stranded or preferably double stranded and may vary in length, depending on the item to be labeled as well as the detection technique utilized in the nucleic acid detection process.

The nucleic acid marker may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid tag usually ranges between about 50 to about 1 kilo bases, more usually about 100 bases to about 800 bases, and preferably 150 bases to about 500 b in length.

The nucleic acid taggant may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

In certain embodiments of the methods of the invention, the nucleic acid taggant is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology.

The optical reporter marker compound may be produced as a solid or liquid, water or oil based, a suspension, an aggregate or the like. The optical reporter marker allows for easy detection of where the optical reporter marker is located on or within the item of interest with basic high intensity light emitting equipment such as a hand-held ultraviolet (UV) lamp, IR emitting diode, hand-held IR laser and the like.

The optical reporter marker also enables the authentication of the tablet and/or the tablet packaging by both confirming that the correct emission spectra/wavelength for the optical reporter particle is detected as well as being able to locate and determine by sequencing if the nucleic acid taggant comprises the correct nucleic acid sequence.

In certain embodiments, the optical reporter marker may camouflage or "hide" a specified nucleic acid tag of verifiable sequence by including extraneous and nonspecific nucleic acid oligomers/fragments, thus making it difficult for unauthorized individuals such as forgers to identify the sequence of the nucleic acid tag. In certain embodiments, the optical reporter marker comprises a specified dsDNA taggant from a known source (i.e. mammal, invertebrate, plant and the like) along with genomic DNA from the corresponding or similar DNA source. The amount of the DNA taggant found in a optical reporter marker compound may vary depending on the item to be authenticated, the duration or shelf-life the taggant needs to be viable (e.g. 1 day, 1 month, 1 year, multiple years) prior to authentication, expected environmental exposure, the detection method to be utilized, and other factors.

The method 200 for authenticating an item further comprises, in event 120, applying or introducing the nucleic acid-linked optical reporter marker to an item of interest in event. The nucleic acid-linked optical reporter marker may be applied in a specific, pre-determined amount or quantity. The tablet or tablet packaging may be labeled with an optical reporter marker throughout the complete item, as a coating over the entire item, or only in a predetermined region or portion of the item. The marker may be applied in liquid solution, liquid dispersion, paste, powder, or other form. Application of the marker may be carried out using an eye-dropper, spoon, spatula, syringe, or other applicator tool. When the item to be authenticated is a solid, a specified amount of optical reporter marker maybe incorporated throughout the volume of the item, or only on the surface of the item or, in some embodiments, placed only on a previously designated section or portion of the item. In embodiments where the item to be authenticated is a fungible powder, the nucleic acid-lined optical reporter may be dispersed throughout the powdered material.

The authentication method 200 further comprises, in event 230, detecting the nucleic acid-linked optical reporter tag associated with the item of interest. Usually the detecting of the optical reporter marker associated with the item occurs after a period of time has lapsed. For example, after tagging the tablet or the tablet packaging, the marked item may be introduced into a supply chain or the item may be placed into service. Frequently, forgers have the best access to items when they are being shipped from the manufacturer/producer to a retail outlet or location. Forgers also have access to the items of interest during maintenance or testing of certain of drug products. Having a method in which the producer of the tablet can track and authenticate items or goods allows for a better monitoring of when and where counterfeit drugs are being replaced with forgeries or otherwise being tampered with.

Detecting the optical reporter particle(s) represents a first level of authentication of the item. When the optical reporter particle is an upconverting phosphor particle, the marker can be detected by a high energy invisible light source such as an infrared laser, which may be hand-held and manipulated by a user, or suitably mounted to allow goods to be positioned in the lamp output. The infrared light is absorbed by the optical reporter particles, which in turn emit light at a wavelength that is characteristic of the optical reporter particle. Various upconverting phosphor compositions that provide selectable output wavelengths are known in the art, as described further below, and may be used with the invention. Once the optical reporter has been located within or on the item of interest, obtaining a sample of the optical reporter marker may occur at event 240.

In event 240, a sample is collected from the tablet or the tablet packaging having the optical reporter marker. In certain embodiments, this may comprise visually inspecting the marker compound found in event 230, and/or scraping, cutting or dissolving a portion of the marked item to obtain a sample for analysis. When the item has entered a supply chain or has been in service, a manufacturer or an authorized individual can collect a sample of the optical reporter marker from the item at any desired point along the supply chain or during the service or routine maintenance of an item where the item is utilized for authentication purposes. The collecting of the sample may be carried out, for example, by wiping the item with a cloth (which may be moistened with solvent) to remove the marker from the item. The sample collecting in other embodiments may be achieved using a cutting, gouging, scraping, abrading, or other sampling tool configured to remove a portion of the item containing the optical reporter marker.

The embodiment of FIG. 2 further comprises analyzing the collected sample for the presence of the nucleic acid taggant in event 250. In many embodiments the analyzing of the collected sample comprises determining the DNA sequence of the nucleic acid taggant, and comparing the determined DNA sequence with a known or reference DNA sequence. The analysis of the sample collected from the item may occur without further purification, but in many embodiments some form of extraction, isolation or purification of the nucleic acid tag obtained in the sample may be required. Details on the extraction, concentration and purification techniques useful for the methods of the invention are described more fully below and also in the examples.

In general, analyzing the sample comprises providing a "detection molecule" configured to the nucleic acid tag. A detection molecule includes but is not limited to a nucleic acid probe and/or primer set which is complementary to at least a portion of the sequence of the nucleic acid taggant, or a dye label or color-producing molecule configured to bind and adhere to the nucleic acid taggant. The detection of the nucleic acid taggant may further comprise amplifying the nucleic acid taggant using PCR, with the detection molecule(s) being primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or fully quantitative authentication results. With the use of real time PCR, results from the analysis of the sample can be completed within 30 minutes to two hours, including extracting or purifying the nucleic acid taggant from the collected sample. Various embodiments of the invention may utilize a wide range of detection methods besides for PCR and real time PCR, such as DNA microarray, fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection. The method utilized to detect the nucleic acid is dependent on the quantity of nucleic acid taggant associated with the optical reporter marker. When only a few copies of NA taggant are collected in the marker sample, high sensitivity techniques such as PCR may be preferable over fluorescent probes.

In event 260 the results of the analysis of the collected sample are reviewed and a query or determination is made as to whether or not the specific nucleic acid taggant was detected in the sample. If the nucleic acid taggant is not found or not detected in the collected sample of the tablet or tablet packaging at event 260, the conclusion at event 270 from the analysis is the that item is not authentic or has been tampered with. If the nucleic acid taggant is detected in the sample at event 260, then the item is verified in event 280 as being authentic.

If a determination is made in event 270 that the tablet or tablets packaging is not authentic, a different, earlier point in the supply or commerce chain may be selected and events 230 through 260 may be repeated. Thus an item from an earlier point in the supply chain would be selected, the optical reporter marker detected, and a sample collected and analyzed. If it is again determined that the item is not authentic or has been otherwise tampered with, then events 230-260 may be repeated with an item selected from yet an earlier point in the supply chain. In this manner, the time and/or location of tampering or counterfeit substitute may be located.

In some embodiments, the quantity or concentration of the nucleic acid taggant within a collected sample can be determined and compared to the initial amount of nucleic acid taggant placed in the item to allow for the detection of fraud caused by diluting the item with inferior products by forgers. In general, such quantitative detection would further comprise, in event 250, providing an internal or external control to evaluate the efficiency of detection from one sample/analysis to the next. The efficiency of detection may be affected by many parameters such as, probe hybridization conditions, molecules or substances in the good which may interfere with detection, and/or primer integrity, enzyme quality, temperature variations for detection methods utilizing PCR. By providing a control, in the detection methods, any variable conditions can be normalized to obtain an accurate final concentration of the nucleic acid taggant in the item.

In certain embodiments a plurality of nucleic acid tags with varying sequences associated with a corresponding plurality of optical reporters may be used in labeling a single item. The different nucleic acid tags can be detected qualitatively by the plurality of optical reporters, each with a different emission wavelength linked to a unique sequenceable nucleic acid taggant.

Compounds Utilized in the Methods of the Invention

The methods of authentication of an item of the invention comprise compounds of the formula I:

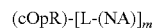

(cOpR)-[L-(NA)]$_m$ wherein:
m is an integer greater than 1;
(cOpR) is a coated optical reporter particle;
(NA) is a nucleic acid oligomer of detectable sequence; and
L is a linking group covalently bound to the coated optical reporter particle and to the nucleic acid oligomer.

While formula I specifically relates to linking nucleic acid oligomers or nucleotides to the surface of the coated optical reporter particle, it should be understood to the those skilled in the art that other biomolecules besides nucleotides can be covalently linked to L. Such biomolecules include but are not limited to peptides, proteins, antibodies, enzymes, DNA binding proteins and the like. These biomolecules, maybe modified to include lipids, carbohydrates, fluorescent and/or upconverting phosphor molecules or other detectable compounds or markers.

In many embodiments, NA is a DNA oligomer. The DNA oligomer maybe either single stranded DNA or double stranded DNA. In certain embodiments NA maybe comprise cDNA, RNA, STR (single tandem repeat) or SNP (single nucleotide polymorphism). NA oligomers of the compositions of the invention may also be modified to comprise at least one dUTP nucleic acid or at least one nucleic acid within the oligomer which has been modified to contain a detectable marker.

In many embodiments NA is a DNA oligomer having a length of between about 40 base pairs and about 1000 base pairs (per strand).

In other embodiments the DNA has a length of between about 80 and 500 base pairs (per strand).

In yet other embodiments the DNA has a length of between about 100 to about 250 base pairs (per strand).

The DNA used with the invention maybe natural or synthetically produced. All or a portion of the DNA may comprise an identifiable sequence.

In certain embodiments of formula I, the coated optical reporter comprises a visible or infrared detectable light emitting material selected from the group consisting of a fluorescent dye, an upconverting phosphor, a ceramic powder, or a quantum dot material. In most embodiments where the cOpR comprises a visible or infrared detectable light emitting material, the light emitting materials are excitable by UV, visible or an infrared light source.

In some embodiments, rare earth-doped ceramic particles are used as phosphor particles. Phosphor particles may be detected by any suitable method, including but not limited to up-converting phosphor technology (UPT), in which up-converting phosphors transfer lower energy infrared (IR) radiation into higher-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEE Proc. Nanobiotechnol. 152(2):64 (2005), each incorporated by reference herein in its entirety.

In many embodiments, the phosphor nanoparticles utilized in the methods of the invention may be of the formula A $$(Y_x RE^1_y RE^2_z)_2 O_3 \quad\quad A$$

wherein:
RE$^1$ and RE$^2$ each is a different rare earth element;
x is from about 0.6 to about 0.95;
y is from 0 to about 0.35; and
z is from 0 0.1 to about 0.001;
provided that y and z are not simultaneously equal to 0.

The rare earth elements RE$^1$ and RE$^2$ may each independently be selected from Ytterbium, Erbium, Holmium, Thulium, or Terbium.

In many embodiments RE$^1$ is Ytterbium.
In many embodiments RE$^2$ is Erbium.

The up-converting particles utilized in the methods of the invention may be spherical, non-agglomerated, non-porous particles with an average size of 40-60 nm. In general, particle sizes may range from about 10 nm to about 5 um in size. Such up-converting phosphor nanopowders such as doped yttrium oxide and yttrium oxysulfide are commercially available and may be obtained from such as Nanocerox, Inc., of Ann Arbor, Mich.

Suitable examples of up-converting phosphors are compounds of rare earths or elements from the group IIIB such as: Na-yttrium fluoride, lanthanum fluoride, lanthanum oxysulphide, yttrium oxysulphide, yttrium fluoride, yttrium gallate, gadolinium fluoride, barium-yttrium fluorides, gadolinium oxysulphide as well as compounds of the above type doped with activator pairs such as ytterbium/erbium, ytterbium/thulium or ytterbium/holmium. Other suitable up-converting phosphors include chelate compounds of erbium, neodymium, thulium, holmium and praseodymium.

The following compositions are merely illustrative of some of the up-converting phosphor containing compositions that can be synthesized by the synthetic reaction schemes of the methods of the present invention. Various modifications to these synthetic reaction schemes can be made and will be suggested to one skilled in the art having referred to the disclosure contained in this application.

TABLE I

Upconverting Phosphor Compositions

| Phosphor Material | Absorber Ion | Emitter Ion |
|---|---|---|
| Oxysulfides (O$_2$S) | | |
| Y$_2$O$_2$S | Ytterbium | Erbium |
| Gd$_2$O$_2$S | Ytterbium | Erbium |
| La$_2$O$_2$S | Ytterbium | Holmium |
| Oxyhalides (OX$_y$) | | |
| YOF | Ytterbium | Thulium |
| Y$_3$OCl$_7$ | Ytterbium | Terbium |
| Fluorides (F$_x$) | | |
| YF$_3$ | Ytterbium | |
| GdF$_3$ | Ytterbium | Erbium |
| LaF$_3$ | Ytterbium | Erbium |
| NaYF$_3$ | Ytterbium | Holmium |
| BaYF$_5$ | Ytterbium | Thulium |
| BaY$_2$F$_8$ | Ytterbium | Thulium |
| Gallates (Ga$_x$O$_y$) | | |
| YGaO$_3$ | Ytterbium | Erbium |
| Y$_3$Ga$_5$O$_{12}$ | Ytterbium | Erbium |
| Silicates (Si$_x$O$_y$) | | |
| YSi$_2$O$_5$ | Ytterbium | Holmium |
| YSi$_3$O$_7$ | Ytterbium | Thulium |

In certain embodiments the coated optical reporter used in the methods of the invention may also comprise at least one electromagnetic emitting material. An electromagnetic emitting material as part of the composition of the invention, allows for the composition to be detected by various methods and devices. Where the electromagnetic emitting material is detectable by mechanical devices which provide at least one source selected from the group consisting of an infrared radiation source, magnetic field source or electromagnetic pulse. This electromagnetic emitting material may be in conjunction with at least one light emitting material, such as an upconverting phosphor.

When the compositions used in the methods of authenticating a tablet or tablet packaging comprise UCPs, the upconverting phosphor material/particle in certain embodiments have the formula B $$Y_x Yb_y Er_z O_2 S \quad\quad B$$

wherein:
x is from about 0.6 to about 0.95;
y is from about 0.05 to about 0.35; and
z is from about 0.1 to about 0.001.

In other embodiments, the upconverting phosphor particle may be of the formula C:

$$Na(Y_xYb_yEr_z)F_4 \qquad C$$

wherein
x is from about 0.6 to about 0.95
y is from about 0.05 to about 0.35; and
z is from about 0.1 to about 0.001.

In certain embodiments of formula I, L comprises an alkylene moiety having a first end covalently bound to the coated optical reporter particle (cOpR) and a second end covalently bound to the nucleic acid oligomer (NA).

In many embodiments of formula I, L is of the formula D:

$$-A-R^1-B- \qquad D$$

wherein:
$R^1$ is $C_{2-8}$alkylene;
-A- is a group covalently bonded to the surface of the coated optical reporter; and
—B— is a group covalently bonded to the 3' or 5' end of the nucleic acid oligomer.

In certain embodiments of formula D, —$R^1$— is —$(CH_2)_n$— and n is from 2 to 8.

In certain embodiments of formula D, —B— is:
—S—;
—O—;
—$NR^a$—;
—S—$(CH_2)_p$—;
—O—$(CH_2)_p$—;
—$NR^a$—$(CH_2)_p$—;
—S—$(CH_2)_q$—C(O)—$NR^a$—$(CH_2)_p$—;
—O—$(CH_2)_q$—C(O)—$NR^a$—$(CH_2)_p$—;
—$NR^a$—$(CH_2)_q$—C(O)—$NR^a$—$(CH_2)_n$—;
—S—C(O)—$(CH_2)_r$—C(O)—$NR^a$—$(CH_2)_p$—;
—O—C(O)—$(CH_2)_r$—C(O)—$NR^a$—$(CH_2)_p$—; or
—NR—C(O)—$(CH_2)_r$—C(O)—$NR^a$—$(CH_2)_p$—;
wherein:
p is from 2 to 8;
q is from 1 to 8;
r is from 2 to 8; and
each $R^a$ is independently hydrogen or a $C_{1-6}$alkyl.

In certain embodiments of formula D, —B— is:
—S—$(CH_2)_q$—C(O)—$NR^a$—$(CH_2)_p$ or
—$NR^a$—C(O)—$(CH_2)_r$—C(O)—$NR^a$—$(CH_2)_p$—;
wherein:
p is from 2 to 8;
q is from 1 to 8;
r is from 2 to 8; and
each $R^a$ is independently hydrogen or a $C_{1-6}$alkyl.

In other embodiments of formula D, —B— is:
—S—$(CH_2)_q$—C(O)—$NR^a$—$(CH_2)_p$ or
—$NR^a$—C(O)—$(CH_2)_r$—C(O)—$NR^2$—$(CH_2)_p$—;
wherein:
p is from 2 to 6;
q is from 1 to 3; and
r is 2 or 3.

In other embodiments of formula D, —B— is
—S—$CH_2$—C(O)—NH—$(CH_2)_6$—
or
—NH—C(O)—$(CH_2)_3$—C(O)—NH—$(CH_2)_6$—.

In certain embodiments of formula D, -A- is —O—.

In many embodiments of formula I, the coated optical reporter (cOpR) is coated with silica. Usually when the coated optical reporter comprises a coating of silica, the silica comprises at least one Si—O bond.

The value of m in formula I will vary according to the surface area of the coated optical reporter and the number of functional groups on the optical reporter surface cable of bonding to -L-. The value of m is always greater than one, and usually greater than 10. Preferably m is greater than 100, and in many embodiments m is greater than $10^3$. In many embodiments m may be, for example, between about 10 and about $10^9$. In certain embodiments m may be from about 100 to about $10^8$. In some embodiments m may be from about $10^3$ to about $10^7$.

In certain embodiments the compositions used in the methods of the invention are of the formula II:

$$(UCP)\text{-}[A\text{-}R^1\text{---}X\text{---}R^2\text{---}C(O)\text{---}NR^a\text{---}R^3\text{-}(DNA)]_m \qquad II$$

wherein:
m is an integer greater than 1;
UCP is an upconverting phosphor particle;
DNA is a single or double stranded deoxyribonucleic acid oligomer;
-A- is a group capable of covalently bonding to the surface of the Upconverting phosphor particle;
$R^1$ is $C_{2-8}$alkylene,
$R^2$ is $C_{1-8}$alkylene or —C(O)—$C_{1-8}$alkylene-;
—X— is —O—, —S— or —$NR^a$—;
$R^3$ is $C_{2-8}$alkylene; and
$R^a$ is hydrogen or $C_{1-6}$alkyl.

In certain embodiments of the invention, the subject composition may be of formula III:

$$(UCP)\text{-}[O\text{---}R^1\text{---}X\text{---}R^2\text{---}C(O)\text{---}NH\text{---}R^3\text{-}DNA]_m \qquad III$$

wherein m, $R^1$, $R^2$, $R^3$, UCP and DNA are as defined herein.

In certain embodiments of the invention, $R^1$ is $C_{2-6}$alkylene.

In certain embodiments of the invention, $R^2$ is $C_{1-6}$alkylene.

In certain embodiments of the invention, $R^3$ is $C_{2-6}$alkylene.

In certain embodiments of the invention, $R^2$ is —C(O)—$C_{2-6}$alkylene-.

In certain embodiments of the invention, $R^1$ is —$(CH_2)_s$— wherein s is from 2 to 6. In some embodiments s is 3.

In certain embodiments of the invention, $R^2$ is —$(CH_2)_t$— wherein t is from 1 to 6. In some embodiments t is 1.

In certain embodiments of the invention, $R^2$ is —C(O)—$(CH_2)_u$— wherein u is from 1 to 6. In some embodiments u is 2 or 3, preferably 2.

In certain embodiments of the invention, $R^3$ is —$(CH_2)_v$— wherein v is from 2 to 6. In some embodiments v is 6.

In certain embodiments of the invention, the subject composition may be of formula IV:

$$(UCP)\text{-}[O\text{---}(CH_2)_s\text{---}S\text{---}(CH_2)_t\text{---}C(O)\text{---}NH\text{---}(CH_2)_v\text{-}(DNA)]_m \qquad IV$$

wherein:
s is from 2 to 6;
v is from 2 to 6;
t is from 1 to 3; and
m, UCP and DNA are as defined herein.

In certain embodiments of the invention, the compositions may be of formula V:

$$(UCP)\text{-}[O\text{---}(CH_2)_s\text{---}NH\text{---}C(O)\text{---}(CH_2)_u\text{---}C(O)\text{---}NH\text{---}(CH_2)_v\text{-}(DNA)]_m \qquad V$$

wherein:
s is from 2 to 6;
v is from 2 to 6;
u is 2 or 3; and
m, UCP and DNA are as defined herein.

In certain embodiments of the invention, the compositions may be of formula VI:

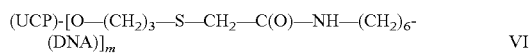
(UCP)-[O—(CH$_2$)$_3$—S—CH$_2$—C(O)—NH—(CH$_2$)$_6$-(DNA)]$_m$  VI wherein m, UCP and DNA are as defined herein.

In certain embodiments of the invention, the compositions may be of formula VII:

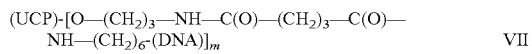
(UCP)-[O—(CH$_2$)$_3$—NH—C(O)—(CH$_2$)$_3$—C(O)—NH—(CH$_2$)$_6$-(DNA)]$_m$  VII wherein m, UCP and DNA are as defined herein.

Encapsulation of a Nucleic Acid Tag

In some embodiments, the nucleic acid marker is incorporated into the product in the presence of molecules which encapsulate the nucleic acid marker by forming microspheres. Encapsulating the nucleic acid marker has the benefit of preventing the nucleic acid marker from degrading while present in a supply chain or during the use of the marked product. The encapsulating materials in most embodiments are of plant origin but may also be synthetically produced materials. The encapsulation of a nucleic acid tag comprises placing the nucleic acid tag into a solvent with a polymer configured to form a microshpere around the tag. The polymers used can be selected from biodegradable or non-biodegradable polymers. Preferred biodegradable polymers are those such as lactic and glycolic acids and esters such as polyanhydrides, polyurethantes, butryic polyacid, valeric polyacid, and the like. Non biodegradable polymers appropriate for encapsulation are vinyletylenene acetate and acrylic polyacid, polyamides and copolymers as a mixture thereof. The polymers can also be selected from natural compounds such as dextran, cellulose, collagen, albumin, casein and the like.

Certain aspects of the invention comprise labeling the microspheres to benefit in the capture of the nucleic acid tag during the extraction of the label from the product of interest. The microspheres may comprise magnetically charged molecules which allow the microspheres containing the nucleic acid tag to be pulled out of a solution by a magnet.

The microspheres can also be labeled with streptavidin, avidin, biotinylated compounds and the like. Labeling the microspheres aids in the purification of the nucleic acid tag prior to detection and also is useful in concentrating the nucleic acid tag so as to enable in some embodiments, the nucleic acid tag to be detected without PCR amplification.

In other embodiments, the nucleic acid marker is applied or added to the product without being encapsulated in microspheres. For example, the nucleic acid marker may be dissolved in a solution compatible with the composition of the particular product such as a textile and then the solution comprising the nucleic acid marker is placed on the surface of the textile product, allowing the nucleic acid marker to be absorbed into the fabric.

Incorporation of the Nucleic Acid Tag into the Particular Tablet or Tablet Packaging The method of incorporating the nucleic acid tag into pharmaceuticals depends significantly on the type of tablet to be authenticated as described above. The nucleic acid tag maybe added to a marker compound in a "naked" or encapsulated form at a predetermine concentration which allows for accurate detection of the nucleic acid taggant. The marker compound is generally a liquid but in certain embodiments maybe a solid. The marker compound maybe initially a liquid and after the addition of the nucleic acid taggant, is dried prior to introducing the marker as an inert substance of a tablet. When the marker compound comprising a nucleic acid taggant is in liquid form, the marker compound is generally applied to the product in a lacquer, paint or liquid aerosol form.

In some embodiments the nucleic acid taggant or tag may be applied to the finished tablet or tablet packaging on a predesignated position. The tablet or tablet packaging is marked in such a manner as to allow detection of an up converting phosphor particle, with minimal quenching of the light emission from the UCP when excited by the appropriate light source. In other embodiments, the NA taggant marker may be introduced to the surface of the tablet as a coating on the tablet or in the capsule material if the drug is in powder form.

The nucleic acid taggant can also be mixed with inert substances compatible with the drug, which are utilized in the manufacturing of the tablet(s) being marked. In this embodiment, the NA taggant is added to the inert substance mixture at an appropriate concentration which allows for adequate detection of the NA marker when formed into a tablet. If the NA taggant marker comprises an UCP composition, the inert substance mixture is compatible with the NA taggant as to not quench the emission of the UCP particle.

Nucleic Acid Tag Extraction and Capture Methods

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In some embodiments, the authentication process comprises capturing the nucleic acid tag directly with a complementary hybridization probe attached to a solid support. In general, the methods for capturing the nucleic acid tag involve a material in a solid-phase interacting with reagents in the liquid phase. In certain aspects, the nucleic acid probe is attached to the solid phase. The nucleic acid probe can be in the solid phase such as immobilized on a solid support, through any one of a variety of well-known covalent linkages or non-covalent interactions. In certain aspects, the support is comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of capturing the nucleic acid tag, a nucleic acid probe can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin are useful. Examples of other functional group linkers include ester, amide, carbamate, urea, sulfonate, ether, and thioester. A 5' or 3' biotinylated nucleotide can be immobilized on avidin or streptavidin bound to a support such as glass.

Depending on the initial concentration of the nucleic acid tag added to the product of interest, the tag can be detected quantitatively without being amplified by PCR. In some embodiments, a single stranded DNA tag labeled with a detection molecule (i.e. fluorophore, biotin, etc.) can be hybridized to a complementary probe attached to a solid support to allow for the specific detection of the "detection molecule" configured to the tag. The nucleic acid DNA tag can also be double stranded, with at least one strand being labeled with a detection molecule. With a dsDNA tag, the nucleic acid tag must be heated sufficiently and then quick cooled to produce single stranded DNA, where at least one of the strands configured with a detection molecule is capable of hybridizing to the complementary DNA probe under appropriate hybridization conditions.

In certain aspects of the invention, the complementary probe is labeled with a detection molecule and allowed to hybridize to a strand of the nucleic acid tag. The hybridization of the probe can be completed within the pill or can be completed after the nucleic acid tag/marker has been extracted from the product, such as when the drug is in liquid form. The direct detection methods described herein depend on having a large initial concentration of nucleic acid label embedded into the pills or rigorous extraction/capture methods which concentrate the nucleic acid tag extracted from a large volume or mass of a particular drug.

In one embodiment, where the NA taggant comprises an up converting particle, the extraction of the NA taggant marker varies depending on the type of tablet/pill being authenticated. When the NA marker comprises a UCP particle, the NA marker can be located by detecting the presence of the UCP by an appropriate light source. The NA marker can then be extracted from the tablet by scraping, cutting out, or dissolving the portion of the tablet which is determined to have the presence of the correct up-converting phosphor particle(s). Once the portion of the item containing the NA marker has been removed the item of interest, the NA marker may be isolated and/or prepared for PCR analysis utilizing techniques known to those skilled in the art of PCR sample preparation.

Real-Time PCR Amplification

In many embodiments, the authentication process comprises amplifying the nucleic tag by polymerase chain reaction. However, conventional PCR amplification is not a quantitative detection method. During amplification, primer dimers and other extraneous nucleic acids are amplified together with the nucleic acid corresponding to the analyte. These impurities must be separated, usually with gel separation techniques, from the amplified product resulting in possible losses of material. Although methods are known in which the PCR product is measured in the log phase, these methods require that each sample have equal input amounts of nucleic acid and that each sample amplifies with identical efficiency, and are therefore, not suitable for routine sample analyses. To allow an amount of PCR product to form which is sufficient for later analysis and to avoid the difficulties noted above, quantitative competitive PCR amplification uses an internal control competitor and is stopped only after the log phase of product formation has been completed.

In a further development of PCR technology, real time quantitative PCR has been applied to nucleic acid analytes or templates. In this method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time. Reverse transcriptase (RT)-real time PCR (RT-PCR) has also been described (Gibson et al., 1996). Numerous commercially thermal cyclers are available that can monitor fluorescent spectra of multiple samples continuously in the PCR reaction, therefore the accumulation of PCR product can be monitored in 'real time' without the risk of amplicon contamination of the laboratory. Heid, C. A.; Stevens, J.; Livak, K. L.; Williams, P. W. (1996). Real time quantitative PCR. Gen. Meth. 6: 986-994.

In some embodiments of the anti-counterfeit authentication process, real time PCR detection strategies may be used, including known techniques such as intercalating dyes (ethidium bromide) and other double stranded DNA binding dyes used for detection (e.g. SYBR green, a highly sensitive fluorescent stain, FMC Bioproducts), dual fluorescent probes (Wittwer, C. et al., (1997) BioTechniques 22: 176-181) and panhandle fluorescent probes (i.e. molecular beacons; Tyagi S., and Kramer FR. (1996) Nature Biotechnology 14: 303-308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques must be practiced to minimize the presence of matrix and contaminant DNA and to prevent primer dimer formation. Appropriate PCR instrument analysis software and melting temperature analysis permit a means to extract specificity and may be used with these embodiments.

PCR amplification is performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe which allow fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye. As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

Molecular beacons systems are frequently used with real time PCR for specifically detecting the nucleic acid template in the sample quantitatively. For instance, the Roche Light Cycler™ or other such instruments may be used for this purpose. The detection molecule configured to the molecular beacon probe may be visible under daylight or conventional lighting and/or may be fluorescent. It should also be noted that the detection molecule may be an emitter of radiation, such as a characteristic isotope.

The ability to rapidly and accurately detect and quantify biologically relevant molecules with high sensitivity is a central issue for medical technology, national security, public safety, and civilian and military medical diagnostics. Many of the currently used approaches, including enzyme linked immunosorbant assays (ELISAs) and PCR are highly sensitive. However, the need for PCR amplification makes a detection method more complex, costly and time-consuming. In certain embodiments anti-counterfeit nucleic acid tags are detected by Surface Enhanced Raman Scattering (SERS) as described in U.S. Pat. No. 6,127,120 by Graham et al. SERS is a detection method which is sensitive to relatively low target (nucleic acid) concentrations, which can preferably be carried out directly on an unamplified samples. Nucleic acid tags and/or nucleic acid probes can be labeled or modified to achieve changes in SERS of the nucleic acid tag when the probe is hybridized to the nucleic acid tag. The use of SERS for quantitatively detecting a nucleic acid provides a relatively fast method of analyzing and authenticating a particular product.

Another detection method useful in the invention is the Quencher-Tether-Ligand (QTL) system for a fluorescent biosensor described in U.S. Pat. No. 6,743,640 by Whitten et al. The QTL system provides a simple, rapid and highly-sensitive detection of biological molecules with structural specificity. QTL system provides a chemical moiety formed of a quencher (Q), a tethering element (T), and a ligand (L). The system is able to detect target biological agents in a sample by observing fluorescent changes.

The QTL system can rapidly and accurately detect and quantify target biological molecules in a sample. Suitable examples of ligands that can be used in the polymer-QTL approach include chemical ligands, hormones, antibodies, antibody fragments, oligonucleotides, antigens, polypeptides, glycolipids, proteins, protein fragments, enzymes, peptide nucleic acids and polysaccharides. Examples of quenchers for use in the QTL molecule include methyl viologen, quinones, metal complexes, fluorescent dyes, and electron accepting, electron donating and energy accepting moieties. The tethering element can be, for example, a single bond, a single divalent atom, a divalent chemical moiety, and a multivalent chemical moiety. However, these examples of the ligands, tethering elements, and quenchers that form the QTL molecule are not to be construed as limiting, as other suitable examples would be easily determined by one of skill in the art.

Kits for Authenticating Items Using Nucleic Acid-Linked Optical Reporters

The invention also provides kits for authenticating tablets and/or the primary and secondary packaging for drugs, using the methods of the invention. The kits of the invention may comprise, for example, a container of the optical reporter marker, and a sample tube for holding a collected sample of the item (tablet or tablet packaging) to be authenticated. The kits may further comprise an applicator for applying a sample of the optical reporter to the item. The kits may still further comprise a collection tool for taking a sample of the labeled item for transfer to the sample tube. The kits may further comprise a portable light source for detecting the optical reporters.

By way of example, the optical reporter marker may be in the form of a liquid solution or dispersion, and the container with the kit would be suitably configured for holding a liquid. The applicator of the kit may comprise an "eye-dropper" for applying liquid optical reporter marker solution to the item in droplet form, a spatula for smearing the solution on an item, a syringe for injecting the solution into an item, or like type of applicator. The collection tool of the kit may comprise a spoon, gouge, a scraping or abrading tool for removing a sample of the labeled item, a blade or scissors for cutting a piece of the item, a cloth (which may be solvent-moistened) for wiping a sample from the item, or the like. The sample tube of the kit may comprise a sealable vial or eppendorf tube, and may contain solvent or solution for extraction of the optical reporter marker from the sample taken from the tagged item. The portable light source of the kit may comprise a hand-held UV lamp suitable for detecting the optical reporter marker.

The kit may further comprise primers and/or probes as well as solutions appropriate for PCR analysis. The kit may further comprise a small PCR instrument for analysis of the extracted optical reporter marker.

The kits of the invention thus provide a convenient, portable system for practicing the methods of the invention.

Synthesis of UCP Particles Covalently Linked to Biomolecules

Nucleotide-labeled optical reporters in accordance with the invention can be made by a variety of methods, including those depicted in the co-pending U.S. application "Methods for linking Optical Reporters to Biomolecules," which is herein incorporated by reference.

Preferred methods for preparing UCP particles covalently linked to DNA are provided in the following Examples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Pharmaceuticals

For the application of verifying authenticity of pharmaceuticals, simplicity is desired.

Referring to FIG. 3, a preferred exemplary DNA tagging system 300 is illustrated. In particular, the labeling of pharmaceutical drugs such a typical uni-dose tablet 302 with nucleic acid material for proof of authenticity is shown. Tablet 302 is also shown in a vertical configuration in tablet 304. It is to be noted that tablet 302 may be coated or uncoated and in fact, tablet 302 is a representative pharmaceutical tablet that can may come in various shapes and sizes, be imprinted with brand marking or be generic.

The tablet 302 is tagged with the DNA in a process similar to those described in FIG. 1. A DNA labeling process 306 prints or marks the tablet 302 either wholly or partially, as it is shown. For example, tablet 302 may be a DNA indicia 308 marked on the surface of the tablet 302. In other embodiments, the entire tablet 302 may be coated with the DNA tag. Once the DNA labeling process is completed, a verification process as illustrated in FIG. 4 may be implemented.

In FIG. 4, the tablet 302 is verified as authentic or counterfeit in a verification process 402. The verification process 402 involves locating the DNA indicia 308 on the tablet and obtaining a sample of the DNA indicia 308. The DNA marker 308 comprises an upconverting phosphor material which is excited by an IR light source, which in turn identifies the location of the DNA indicia 308 on the tablet. The sample of the DNA marker 308 is analyzed with RT PCR and specific primers to a predetermined DNA sequence to determine if the DNA marker 308 is capable of forming amplicons. If a PCR product is formed the tablet is considered authentic. If no PCR product is produced, the tablet is counterfeit.

Example 2

Up-converting phosphor nanopowder (doped yttrium oxide and yttrium oxysulfide upconverting particles) were obtained from Nanocerox, Inc., Ann Arbor, Mich.

ABBREVIATIONS

UCP Up converting phosphor
UTP Up converting phosphor technology
OpR optical reporter particle
cOpR coated optical reporter particle
TEOS tetraethoxysilane, tetraethyl orthosilicate; ethyl silicate; silicic acid, tetraethyl ester; or silicon ethoxide
MOS methyl oxysilane
EOS ethyl oxysilane
POS propyl oxysiline
NHS N-Hydroxsuccinimde
IOA Iodoacetamide
DIPCI Diisopropylcarbodiimide
DCM dichloromethane/methylene chloride
DIPEA diisopropyl ethylamine
DMF N,N-dimethylformamide
DMAP 4-dimethylaminopyridine
ECDI 1-ethyl-3-(3'-dimethylaminopropyl)carbodiimide
EtOAc ethyl acetate
EtOH ethanol
hplc high performance liquid chromatography
mCPBA m-chloroperbenzoic acid
MeCN acetonitrile
TLC thin layer chromatography
Doped Yttrium Oxysulfide with Oxypropylsulfanylacetamide-Linked DNA The synthetic procedure of this Example is shown below in Scheme A.

SCHEME A

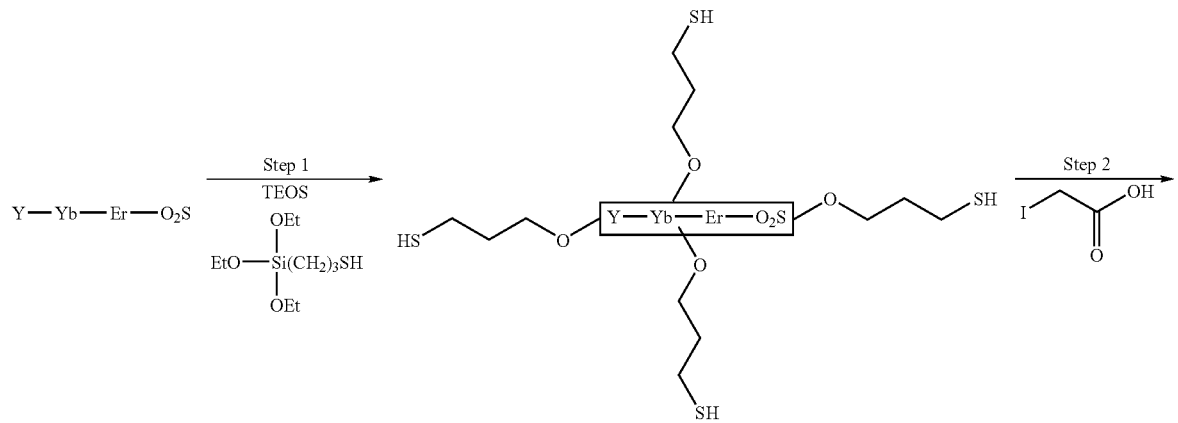

-continued
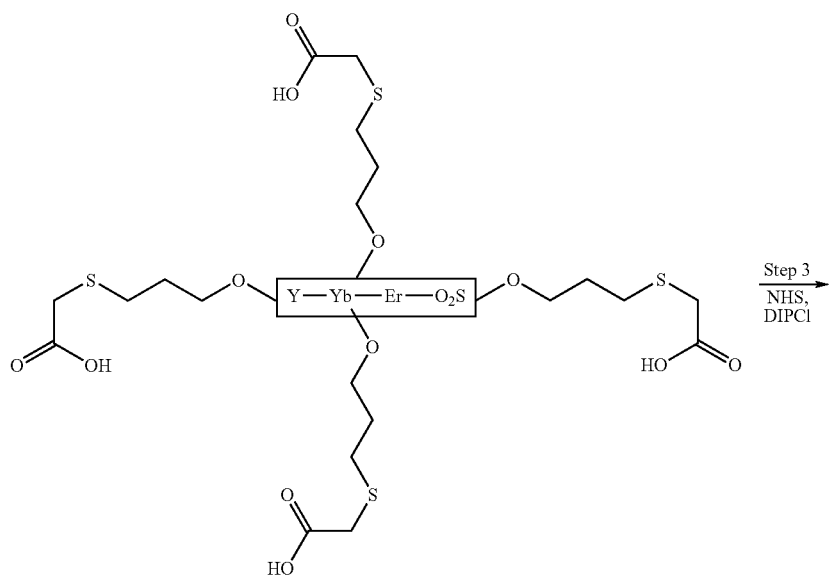
$\xrightarrow{\text{Step 3} \atop \text{NHS, DIPCl}}$
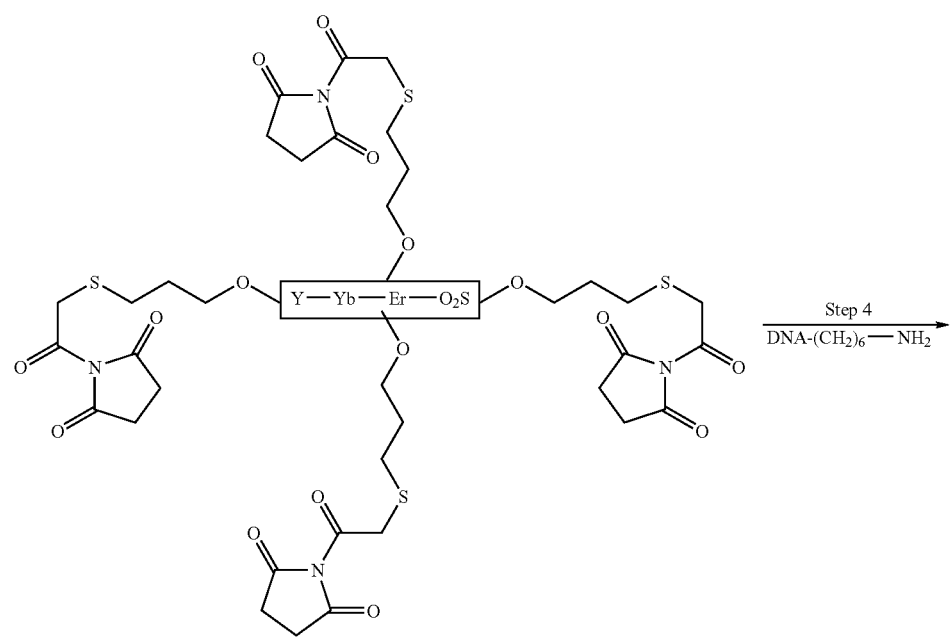
$\xrightarrow{\text{Step 4} \atop \text{DNA-(CH}_2)_6-\text{NH}_2}$ -continued

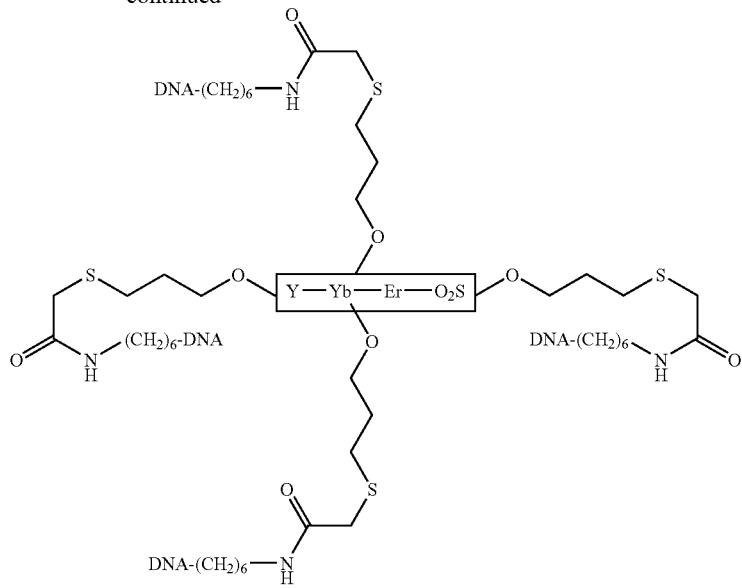

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.

Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Taq mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted $1/10$, $1/100$, and $1/1000$, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

The results from the RT-PCR experiment where similar to those shown in FIG. 5, discussed below in Example 3.

Example 3

Doped Yttrium Oxysulfide with (oxy-propylamino)-acetic acid 5-amino-4-oxo-pentyl ester-linked DNA The synthetic procedure of this example is shown below in Scheme B.

SCHEME B

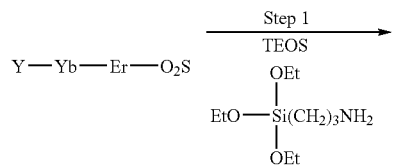

-continued
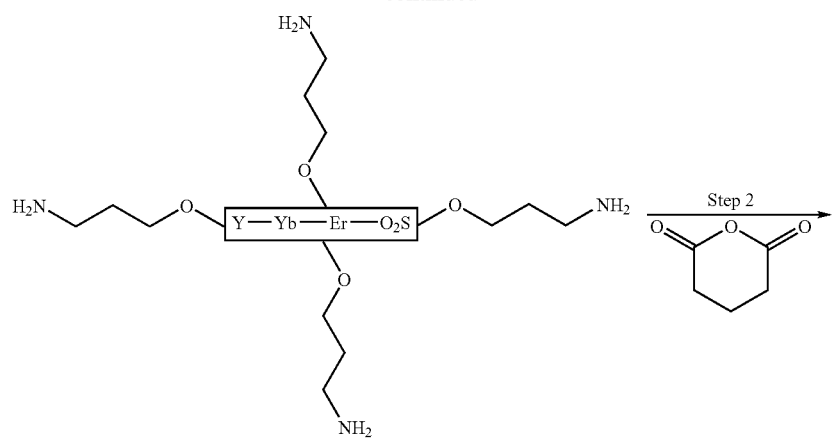
Step 2
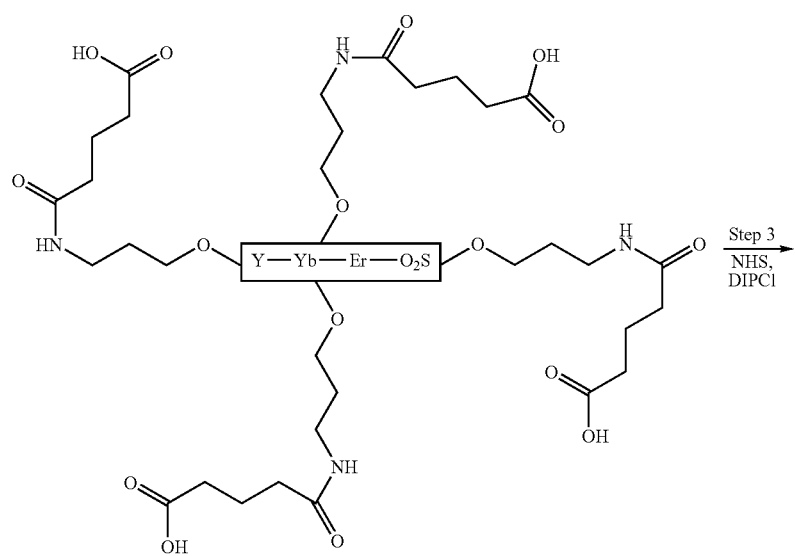
Step 3
NHS, DIPCl
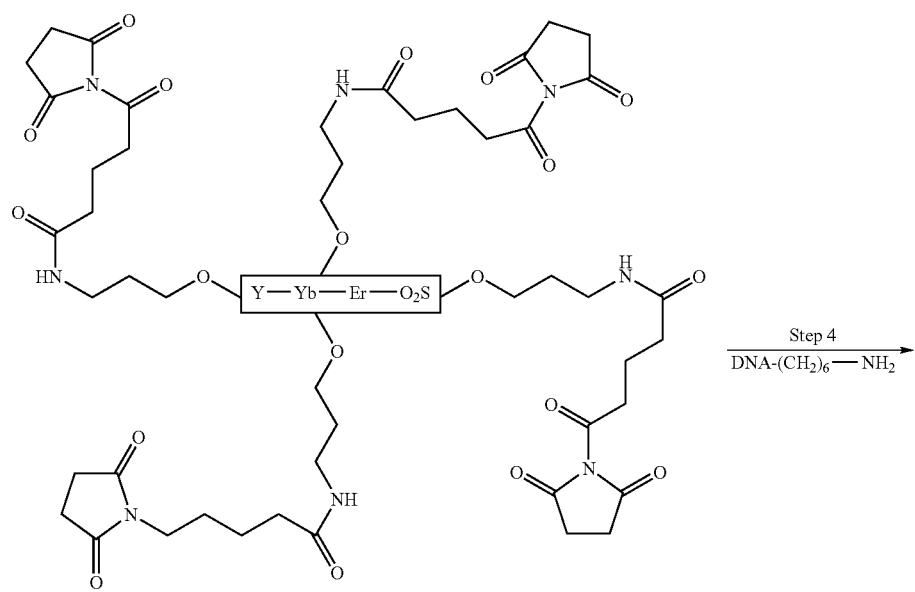
Step 4
DNA-(CH₂)₆—NH₂

-continued

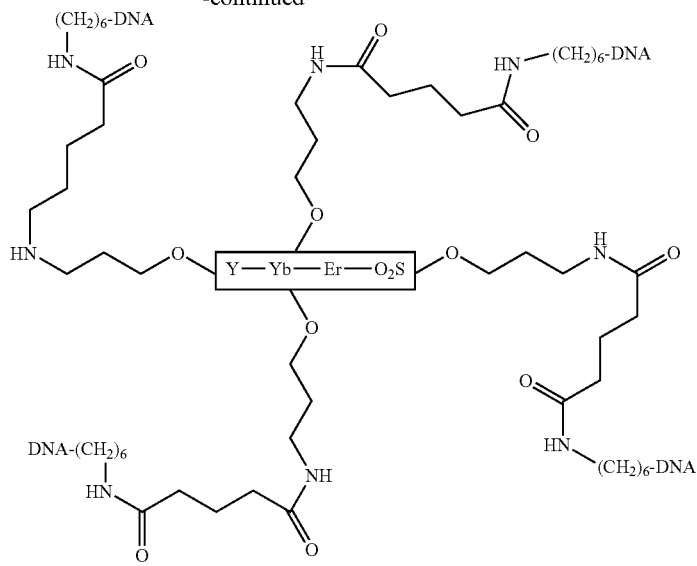

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.
Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Taq mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted $1/10$, $1/100$, and $1/1000$, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

Figure 5:
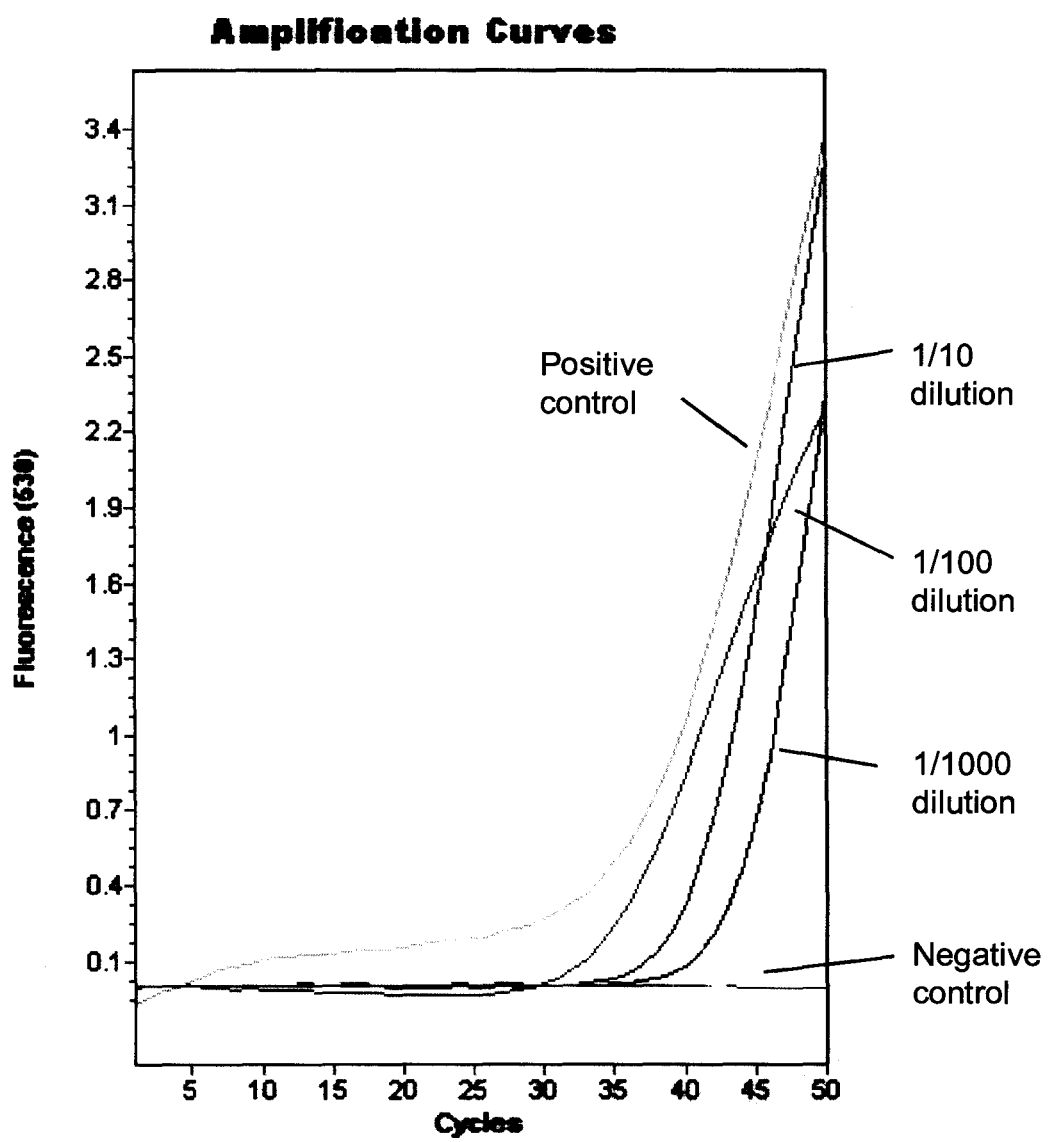
FIG. 5 is a plot of a real-time PCR results for a composition of the invention, comprising an optical reporter linked to a sequenceable DNA molecule.

The results from the RT-PCR experiment are shown in FIG. 5. The results in FIG. 5 show that the $1/100$ dilution sample had a Ct of 30, while the $1/10$ and $1/1000$ dilution had a Ct of 33 and Ct of 36, respectively. At the $1/10$ dilution the concentration of the UCP particles is high enough to quench the PCR signal, thus delaying the cycle in which amplification of the target DNA is present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. The method for authenticating a tablet comprising the steps of:
   providing an optical reporter marker, the optical reporter marker having at least one light emitting upconverting phosphor particle linked by a linking group comprising an alkylene moiety, to a nucleic acid material, the nucleic acid material having a plurality of polymorphic double stranded (ds) DNA fragments, said polymorphic dsDNA fragments each having an artificial sequence obtained by digestion and ligation of extracted DNA,
   applying the optical reporter marker to the tablet of interest,
   detecting the optical reporter marker associated with the tablet with a light source,
   obtaining a sample of the optical reporter marker from the tablet of interest for analysis,
   analyzing the collected sample to detect the presence of the identifiable portion of the polymorphic (ds)DNA fragments linked to the upconverting phosphor particle by performing a polymerase chain reaction (PCR) on the collected sample comprising said non-heritable polymorphic (ds)DNA fragments using specific primers, thereby producing specific length amplicons; and
   verifying that the tablet is genuine by detecting the specific length amplicons amplified from said polymorphic dsDNA fragments in said tablet.

2. The method of claim 1, wherein the optical reporter marker has the composition of the formula I:

$$(cOpR)\text{-}[L\text{-}(NA)]_m \qquad I$$

wherein:
   m is an integer greater than 1;
   (cOpR) is a coated optical reporter particle, said COpR having an upconverting phosphor (UCP) material;
   (NA) is a nucleic acid oligomer of detectable sequence, wherein (NA) is a double stranded DNA molecule having a length of between 40 base pairs and 1000 base pairs; and
   L is the linking group having an alkylene moiety and being covalently bound to the coated optical reporter particle and to the nucleic acid oligomer.

3. The method of claim 2, wherein (NA) is a double stranded DNA molecule having a length of between about 100 base pairs and about 800 base pairs.

4. The method of claim 2, wherein L comprises an alkylene moiety, and having a first end covalently bound to the coated optical reporter particle and a second end covalently bound to the nucleic acid oligomer.

5. The method of claim 1, wherein (UCP) is an upconverting phosphor particle of the formula:

$$Y_x Yb_y Er_z O_2 S;\text{ or}$$

$$Na(Y_x Yb_y Er_z)F_4;$$

wherein:
   x is from about 0.6 to about 0.95;
   y is from about 0.05 to about 0.35; and
   z is from about 0.1 to about 0.001.

6. The method of claim 2, wherein L is of the formula:

$$\text{-A-R}^1\text{—B—}$$

wherein:
   $R^1$ is $C_{2-8}$alkylene;
   -A- is a group covalently bonded to the surface of the coated optical reporter; and
   —B— is a group covalently bonded to the 3' or 5' end of the nucleic acid oligomer.

7. A method for authenticating a tablet comprising the steps of;
   providing a tablet comprising an optical reporter marker, the optical reporter marker having at least one light emitting upconverting phosphor particle linked by a linking group comprising an alkylene moiety, to a nucleic acid taggant, the nucleic acid taggant having a plurality of polymorphic double stranded (ds) DNA fragments, said polymorphic dsDNA fragments each having an artificial sequence obtained by digestion and ligation of extracted DNA,
   detecting the optical reporter marker associated with the tablet with a light source,
   obtaining a sample of the optical reporter marker from the tablet for analysis,
   analyzing the collected sample to detect the presence of the identifiable portion of the polymorphic (ds)DNA fragments linked to the upconverting phosphor particle by performing a polymerase chain reaction (PCR) on the collected sample comprising said polymorphic (ds) DNA fragments using specific primers, thereby producing specific length amplicons; and
   verifying that the tablet is genuine by detecting the specific-length amplicons amplified from said polymorphic dsDNA fragments in said tablet.

8. The method of claim 7, wherein the optical reporter marker has the composition of the formula I:

$$(cOpR)\text{-}[L\text{-}(NA)]_m \qquad I$$

wherein:
   m is an integer greater than 1;
   (cOpR) is a coated optical reporter particle, said COpR having an upconverting phosphor (UCP) material;
   (NA) is a nucleic acid oligomer of detectable sequence, wherein (NA) is a double stranded DNA molecule having a length of between 40 base pairs and 1000 base pairs; and L is the linking group comprising an alkylene moiety, and being covalently bound to the coated optical reporter particle and to the nucleic acid oligomer.

9. The method of claim 8, wherein (NA) is a double stranded DNA molecule having a length of between about 100 base pairs and about 800 base pairs.

10. The method of claim 8, wherein L comprises a $C_{2-8}$ alkylene moiety, and having a first end covalently bound to the coated optical reporter particle and a second end covalently bound to the nucleic acid oligomer.

11. The method of claim 8, wherein (UCP) is an upconverting phosphor particle of the formula:

$Y_xYb_yEr_zO_2S$; or $Na(Y_xYb_yEr_z)F_4$;

wherein:
x is from about 0.6 to about 0.95;
y is from about 0.05 to about 0.35; and
z is from about 0.1 to about 0.001.

12. The method of claim 8, wherein L is of the formula:

-A-$R^1$—B— wherein:
$R^1$ is $C_{2-8}$alkylene;
-A- is a group covalently bonded to the surface of the coated optical reporter; and
—B— is a group covalently bonded to the 3' or 5' end of the nucleic acid oligomer.

13. The method of claim 12, wherein -A- is —O—.

14. The method of claim 12, wherein —$R^1$— is —$(CH_2)_n$— and wherein n is from 2 to 8.

15. The method of claim 12, wherein —B— is:
—S—;
—O—;
—$NR^a$—;
—S—$(CH_2)_p$—;
—O—$(CH_2)_p$—;
—$NR^a$—$(CH_2)_p$—;
—S—$(CH_2)_q$—C(O)—$NR^a$—$(CH_2)_p$—;
—O—$(CH_2)_q$—C(O)—$NR^a$—$(CH_2)_p$—;
—$NR^a$—$(CH_2)_q$—C(O)—$NR^a$—$(CH_2)_p$—;
—S—C(O)—$(CH_2)_r$—C(O)—$NR^a$—$(CH_2)_p$—;
—O—C(O)—$(CH_2)_r$—C(O)—$NR^a$—$(CH_2)_p$—; or
—$NR^a$—C(O)—$(CH_2)_r$—C(O)—$NR^a$—$(CH_2)_p$—;

wherein:
p is from 2 to 8;
q is from 1 to 8;
r is from 2 to 8; and
each $R^a$ is independently hydrogen or $C_{1-6}$alkyl.

16. The method of claim 12, wherein —B— is:
—S—$(CH_2)_q$—C(O)—NH—$(CH_2)_p$ or
—$NR^a$—C(O)—$(CH_2)_r$—C(O)—$NR^a$—$(CH_2)_p$—;

p is from 2 to 6;
q is from 1 to 3; and
r is 2 or 3.

17. The method of claim 12, wherein —B— is:
—S—$CH_2$—C(O)—NH—$(CH_2)_6$—; or
—NH—C(O)—$(CH_2)_3$—C(O)—NH—$(CH_2)_6$—.

18. The method of claim 8, wherein the cOpR is coated with silica.

19. The method of claim 18, wherein cOpR is a coated optical reporter particle having an upconverting phosphor (UCP) material comprising Yttrium oxysulfide.

20. The method of claim 7, wherein the optical reporter marker has the composition of the formula II:

$$(UCP)\text{-}[A\text{-}R^1\text{—}X\text{—}R^2\text{—}C(O)\text{—}NR^a\text{—}R^3\text{-}(DNA)]_m \qquad II$$

wherein:
m is an integer greater than 1;
UCP is an upconverting phosphor particle;
DNA is a single or double stranded deoxyribonucleic acid fragment;
-A- is a group capable of covalently bonding to the surface of the Upconverting phosphor particle;
$R^1$ is $C_{2-8}$alkylene,
$R^2$ is $C_{1-8}$alkylene or —C(O)—$C_{1-8}$alkylene-;
—X— is —O—, —S— or —$NR^a$—;
$R^3$ is $C_{2-8}$alkylene; and
$R^a$ is hydrogen or $C_{1-6}$alkyl.

21. The method of claim 20, wherein the optical reporter marker has the composition of the formula IV:

$$(UCP)\text{-}[O\text{—}(CH_2)_s\text{—}S\text{—}(CH_2)_t\text{—}C(O)\text{—}NH\text{—}(CH_2)_v\text{-}(DNA)]_m \qquad IV$$

wherein:
s is from 2 to 6;
v is from 2 to 6; and
t is from 1 to 3.

22. The method of claim 20, wherein the optical reporter marker has the composition of the formula V:

$$(UCP)\text{-}[O\text{—}(CH_2)_s\text{—}NH\text{—}C(O)\text{—}(CH_2)_u\text{—}C(O)\text{—}NH\text{—}(CH_2)_v\text{-}(DNA)]_m \qquad V$$

wherein:
s is from 2 to 6;
v is from 2 to 6; and
u is 2 or 3.

23. The method of claim 20, wherein the optical reporter marker has the composition of the formula VI:

$$(UCP)\text{-}[O\text{—}(CH_2)_3\text{—}S\text{—}CH_2\text{—}C(O)\text{—}NH\text{—}(CH_2)_6\text{-}(DNA)]_m \qquad VI.$$

24. The composition of claim 20, wherein the composition is of the formula VII:

$$(UCP)\text{-}[O\text{—}(CH_2)_3\text{—}NH\text{—}C(O)\text{—}(CH_2)_3\text{—}C(O)\text{—}NH\text{—}(CH_2)_6\text{-}(DNA)]_m \qquad VII.$$

25. The composition of claim 8, wherein the cOpR comprises a visually detectable light emitting material selected from the group consisting of a fluorescent dye, a upconverting phosphor, a rare earth doped-ceramic powder, and a quantum dot.

26. The composition of claim 25, where said light emitting materials are excitable by UV or infrared light.

27. The method of claim 8, wherein the cOpR comprises at least one electromagnetic radiation emitting material.

28. The composition of claim 27, where the electromagnetic radiation emitting material is detectable by a device which provides a source selected from the group consisting of an infrared radiation source, magnetic field source, a quantum dot or electromagnetic pulse source.

29. The method of claim 2, wherein verifying that the tablet is genuine by detecting said polymorphic dsDNA fragments in said tablet, comprises analyzing the specific lengths of said specific length amplicons with capillary electrophoresis.

30. The method of claim 12, wherein verifying that the tablet is genuine by detecting said polymorphic dsDNA fragments in said article, comprises analyzing the specific length amplicons amplified from said polymorphic (ds)DNA fragments with capillary electrophoresis.

* * * * *